US008563507B2

(12) United States Patent
Upton et al.

(10) Patent No.: US 8,563,507 B2
(45) Date of Patent: Oct. 22, 2013

(54) METHOD OF TREATING A DISEASE OR CONDITION CHARACTERIZED BY ABERRANT EPITHELIAL CELL PROLIFERATION

(75) Inventors: Zee Upton, Queensland (AU); Jennifer Ann Kricker, Queensland (AU)

(73) Assignee: Queensland University of Technology, Brisbane (AU)

( * ) Notice: Subject to any disclaimer, the term of this patent is extended or adjusted under 35 U.S.C. 154(b) by 0 days.

(21) Appl. No.: 12/837,992

(22) Filed: Jul. 16, 2010

(65) Prior Publication Data
US 2010/0279927 A1 Nov. 4, 2010

Related U.S. Application Data

(60) Continuation of application No. 11/807,476, filed on May 29, 2007, now Pat. No. 7,785,835, which is a division of application No. 10/380,892, filed as application No. PCT/AU01/01196 on Sep. 24, 2001, now Pat. No. 7,514,398.

(30) Foreign Application Priority Data

Sep. 22, 2000 (AU) .................................. PR 0309

(51) Int. Cl.
A61K 38/30 (2006.01)
C07K 14/65 (2006.01)
A61P 35/00 (2006.01)

(52) U.S. Cl.
USPC .............................. 514/8.7; 514/8.6; 514/19.3

(58) Field of Classification Search
None
See application file for complete search history.

(56) References Cited

U.S. PATENT DOCUMENTS

| | | |
|---|---|---|
| 5,187,151 A | 2/1993 | Clark et al. |
| 5,407,913 A | 4/1995 | Sommer et al. |
| 5,514,706 A | 5/1996 | Ambler et al. |
| 5,580,955 A | 12/1996 | Nur-E-Kamal et al. |
| 5,830,504 A | 11/1998 | Vuori et al. |
| 7,514,398 B2 | 4/2009 | Upton et al. |

FOREIGN PATENT DOCUMENTS

WO    WO 00/55206    9/2000

OTHER PUBLICATIONS

Yu et al., J. Natl. Cancer Inst. 91: 151-156, 1999.*
Renehan et al., Lancet 363: 1346-1353, 2004.*
Kurek et al., BJU International 85: 125-129, 2000.*
Jasonmi et al., Frontiers in Biosc. 1: G24-29, 1996.*
Moorehead et al., Oncogene 22:853-857, 2003.*
Firth et al., "Structural Determinants of Ligand and Cell Surface Binding of Insulin-Like Growth Factor-Binding Protein-3", *The Journal of Biological Chemistry*, 273: 2631-2638, 1998.
Francois et al., "Vitronectin Interaction with Glycosaminoglycans", *The Journal of Biological Chemistry*, 274:37611-37619, 1999.
Gui et al., "Insulin-Like Growth Factor (IGF)-Binding Protein-3 (IGFBP-3) Binds to Fibronectin (FN): Demonstration of IGF-I/IGFBP-3/FN Ternary Complexes in Human Plasma", *J. Clin. Endocrinol. Metab*, 86:2104-2110, 2001.
Jones et al., "Cell Migration: Interactions Among Integrins, IGFs and IGFBPs", *Progress in Growth Factor Research*, 6:319-327, 1995.
Jones et al., "Extracellular Matrix Contains Insulin-Like Growth Factor Binding Protein-5: Potentiation of the Effects of IGF-I", *The Journal of Cell Biology*, 121:679-687, 1993.
Jones et al., Ligand Occupancy of the aVβ3 Integrin is Necessary for Smooth Muscle Cells to Migrate in Response to Insulin-Like Growth Factor I, *Proc. Natl. Acad. Sci. USA*, 93:2482-2487, 1996.
Klemke et al., "Receptor Tyrosine Kinase Signaling Required for Integrin avβ5-Directed Cell Motility but Not Adhesion on Vitronectin", *The Journal of Cell Biology*, 127:859-866, 1994.
Loskutoff et al., "Regulation of Cell Adhesion by PAI-1", *APMIS*, 207:54-61, 1999.
Martin et al., 4th International Workshop on IGF Binding Proteins, Growth Hormone & IGF Research 2000, p. A23.
Mousa et al., "Role of Hypoxia and Extracellular Matrix-Integrin Binding in the Modulation of Angiogenic Growth Factors Secretion by Retinal Pigmented Epithelial Cells", *Journal of Cellular Biochemistry*, 74:135-143, 1999.
Rousselle et al., "Potential Synergies Between Matrix Proteins and Soluble Factors on Resorption and Proteinase Activities of Rabbit Bone Cells", *Histol. Histopathol.*,16:727.734, 2001.
Taraboletti et al., "The 140-Kilodalton Antiangiogenic Fragment of Thrombospondin-1 Binds to Basic Fibroblast Growth Factor", *Cell Growth and Differentiation*, 8:471-479, 1997.
Utpon et al., "Identification of Vitronectin as a Novel Insulin-Like Growth Factor-II Binding Protein",*Endocrinology*, 140:2928-2931, 1999.

* cited by examiner

*Primary Examiner* — Gyan Chandra
(74) *Attorney, Agent, or Firm* — Tarolli, Sundheim, Covell & Tummino LLP

(57) ABSTRACT

An isolated protein complex is provided which includes a growth factor, growth factor binding protein and vitronectin. Preferably, the isolated protein complex includes an insulin-like growth factor-I, insulin-like growth factor binding protein-3 or insulin-like growth factor binding protein-5 and vitronectin. Also provided are methods of modulating cell proliferation and/or migration by administering said protein complex for the purposes of wound healing, skin repair and tissue replacement therapy. Conversely, by using agents that disrupt growth factor protein complexes formed in vivo, growth factor-driven cell proliferation and/or migration may be suppressed such as for the purposes of treating cancers, psoriasis, atherosclerosis and wounds prone to hypertrophic scarring.

8 Claims, 14 Drawing Sheets

(a)

(b)

A

B

C

D

E

F (a)

(b)

A

B

C

D

E

F

Figure 1:
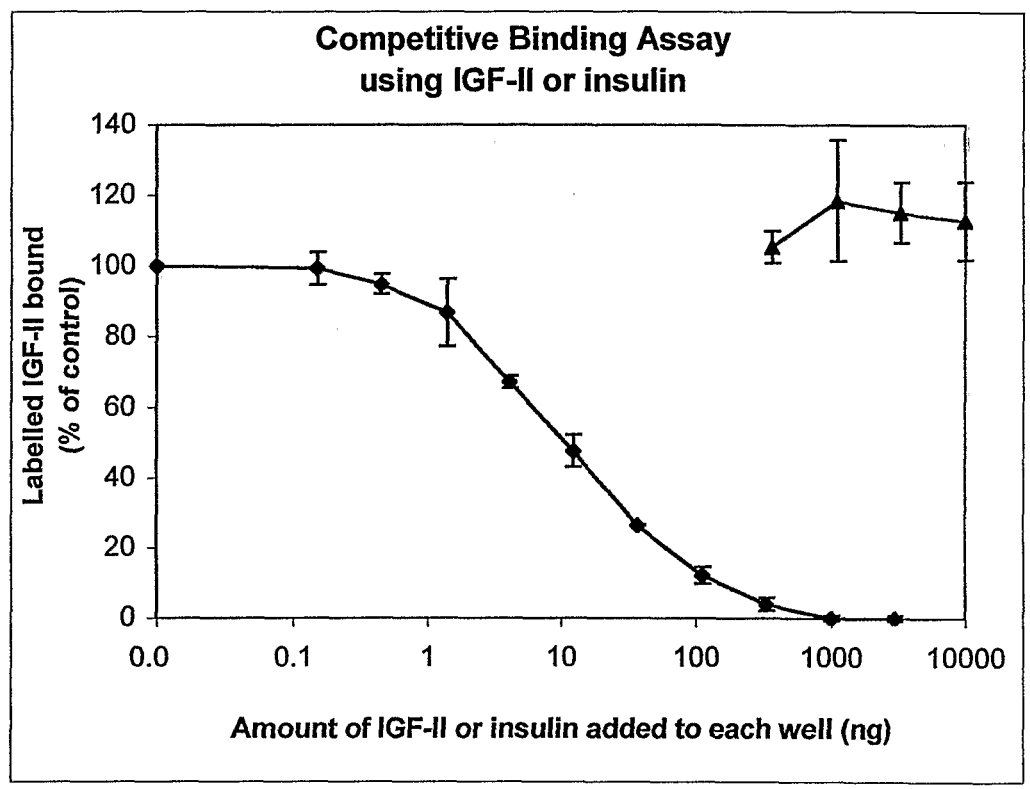

METHOD OF TREATING A DISEASE OR CONDITION CHARACTERIZED BY ABERRANT EPITHELIAL CELL PROLIFERATION

CROSS-REFERENCES TO RELATED APPLICATIONS

This application is a Continuation of U.S. patent application Ser. No. 11/807,476, filed May 29, 2007 now U.S. Pat. No. 7,785,835 which is a Divisional of U.S. patent application Ser. No. 10/380,892, filed Oct. 16, 2003 (now U.S. Pat. No. 7,514,398) which corresponds to PCT International Application No. PCT/AU2001/001196, filed Sep. 24, 2001 and Australian Patent Application No. PR 0309, filed Sep. 22, 2000. The present application claims priority to the aforementioned patent applications, which are incorporated in their entirety herein by reference for all purposes.

FIELD OF THE INVENTION

THIS INVENTION relates to an isolated protein complex which includes a growth factor binding protein and vitronectin. In particular, this invention relates to an isolated protein complex which includes an insulin-like growth factor, an insulin-like growth factor binding protein and vitronectin. Also provided by the invention are growth factor complexes comprising variant growth factors and/or growth factor binding proteins that facilitate or enhance formation of the growth factor complexes. This invention also provides methods of modulating cell proliferation and/or migration by administering said protein complex for the purposes of wound healing, skin repair, cosmetic skin maintenance and tissue replacement therapy. Conversely, by disrupting protein complexes formed in vivo, growth factor-driven cell proliferation and/or migration can be suppressed such as for the purposes of treating cancers, psoriasis, atherosclerosis and wounds prone to hypertrophic scarring. These treatments may have medical and veterinary applications.

BACKGROUND OF THE INVENTION

Skin growth, repair and healing are subject to complex biological control mechanisms which act via both positive and negative signals. Such signals act at the level of controlling cell proliferation, differentiation and migration, and are typically mediated by growth factor polypeptides. In this regard, important growth factors include epidermal growth factor (EGF) and insulin-like growth factors (IGF-I and -II).

Human IGF-I has been reported to exert a wide range of biological activities including stimulation of cell proliferation, differentiation and migration, protection from protein degradation and apoptosis, as well as regulation of endocrine factors such as growth hormone. IGF-II has similar properties to IGF-I but appears to be more relevant to carcinogenesis and fetal and embryonic development, IGF-I having a greater role in postnatal development.

Both IGF-I and IGF-II act through a binding interaction with the type I IGF receptor (IGFR). The availability of the IGFs for such an interaction is regulated by insulin like growth factor binding proteins (IGFBPs 1-6). IGFBPs are known to both positively and negatively regulate IGF function as well as exhibit IGF-independent activity.

Another functional component of IGF pathways is the type II IGFR which is also known as the cation-independent mannose-6-phosphate receptor (CI-MPR). The type II IGFR is a multifunctional protein that binds lysosomal enzymes bearing mannose-6-phosphate moieties, as well as IGF-II, although the functional significance of IGF-II binding is unclear (O'Dell & Day, 1998, Int. J. Biochem. Cell Biol. 30 767; Braulke, 1999, Horm. Metab. Res. 31 242; Nykjaer et al., 1998, J. Cell. Biol. 141 815).

The IGFs have also been reported to bind another group of proteins termed "IGFBP-related proteins" which share structural similarity and include connective tissue growth factor (CTGF) and products encoded by the mac25, nov and cyr61 genes. These bind IGFs with much lower affinity than do IGFBPs.

More recently, vitronectin (VN) has been identified as an extracellular matrix protein, structurally unrelated to IGFBPs and IGFBP-related proteins, that binds IGF-II but not IGF-I (Upton et al., 1999, Endocrinol. 140 2928).

Vitronectin is an ~75 kD, glycosylated extracellular matrix protein which is also found in blood, and has been implicated in cancers, bone diseases and pathological disorders involving angiogenesis (reviewed in Schvartz et al., 1999, Int. J. Biochem. Cell Biol. 31 539). The role of vitronectin in events such as angiogenesis and tumorigenesis at least partly resides in the ability of vitronectin to bind integrins and to interact with components of the urokinase plasminogen activator system (for example PAI-1, uPAR, plasminogen) to thereby promote cell proliferation, adhesion, spreading and migration. Vitronectin has more specifically been implicated in preventing tumor cell apoptosis in response to drug treatment (Uhm et al., 1999, Clin. Cancer Res. 5 1587). Vitronectin appears to be a carrier of IGF-II in the circulation (McMurtry et al., 1996, J. Endocrinol. 150 149).

OBJECT OF THE INVENTION

The present inventor has surprisingly discovered that IGFBPs bind vitronectin, and that IGF-1 can bind vitronectin when bound to an IGFBP.

It is therefore an object of the invention to provide an isolated IGFBP and vitronectin-containing complex.

SUMMARY OF THE INVENTION

In a first aspect, the invention provides an isolated polypeptide complex comprising a growth factor binding protein and vitronectin.

Preferably, the isolated polypeptide complex further comprises a growth factor.

A preferred growth factor is insulin-like growth factor-I (IGF-I).

Other growth factors include epidermal growth factor (EGF), fibroblast growth factor (FGF), basic fibroblast growth factor (bFGF), osteopontin, thrombospondin-1, tenascin-C, PAI-1, plasminogen, fibrinogen, fibrin and transferrin.

A preferred growth factor binding protein is an insulin-like growth factor binding protein selected from the group consisting of IGFBP1, IGFBP2, IGFBP3, IGFBP4, IGFBP5 and IGFBP6.

A more preferred insulin-like growth factor binding protein is IGFBP2, IGFBP3, IGFBP4 or IGFBP5.

An even more preferred insulin-like growth factor binding protein is IGFBP3 or IGFBP5.

In a second aspect, the invention provides an isolated protein complex comprising an IGFBP-related protein and vitronectin.

Preferably, the isolated polypeptide complex further comprises a growth factor, preferably IGF-I.

In one embodiment, the IGFBP-related protein is selected from the group consisting of connective tissue growth factor (CTGF), a polypeptide encoded by the mac25 gene, a polypeptide encoded by the nov gene and a polypeptide encoded by the cyr61 gene.

In a third aspect, the invention provides a isolated protein complex comprising vitronectin, a variant growth factor and/or a variant growth factor binding protein.

In one embodiment, the isolated protein complex of this aspect comprises vitronectin and a variant growth factor engineered to include a heparin binding domain (HBD).

In another embodiment, the isolated protein complex of this aspect comprises vitronectin and a non-glycosylated growth factor binding protein.

In yet another embodiment, the isolated protein complex of this aspect comprises vitronectin and a variant growth factor selected from the group consisting of des(1-6)IGF-II and des(1-3)IGF-I.

Also contemplated according to the first- second- and third-mentioned aspects is that the isolated protein complex of the invention may further include an acid-labile subunit, a polypeptide which can complex with an IGFBP, referred to hereinafter as ALS.

The invention according to the first-, second- and third-mentioned aspects also contemplates isolated protein complexes comprising variants and biologically-active fragments of growth factors, growth factor binding proteins, IGFBP-related proteins and vitronectin, and use of such complexes. Biologically-active fragments and variants include within their scope analogues, mutants, agonists and antagonists of said growth factors, growth factor binding proteins, IGFBP-related proteins and vitronectin.

In a fourth aspect, the invention provides a pharmaceutical composition comprising one or more isolated protein complexes according to the first-, second- or third-mentioned aspect and a pharmaceutically-acceptable carrier or diluent.

In a fifth aspect, the invention provides a pharmaceutical composition comprising a expression construct comprising one or more nucleic acids encoding an isolated protein complex according to the first-, second- or third-mentioned aspect and a pharmaceutically-acceptable carrier or diluent.

In a sixth aspect, the invention provides a transformed cell capable of expressing a recombinant protein complex, or recombinant proteins capable of forming said complex, according to the first-, second- or third-mentioned aspects.

In a seventh aspect, the invention provides a method of modulating cell proliferation and/or migration including the step of administering to an animal or isolated cells thereof, an isolated protein complex according to the first-, second- or third-mentioned aspects.

Preferably, the isolated protein complex comprises an IGFBP and vitronectin.

Preferably, the isolated protein complex further comprises IGF-I.

In an eighth aspect, the invention provides a method of modulating cell proliferation and/or migration, including the step of administering to an animal or isolated cells thereof an agent which prevents or disrupts formation of a protein complex according to the first-, second- or third-mentioned aspects.

Preferably, the agent prevents or disrupts an interaction between an IGFBP and vitronectin.

More preferably, the agent prevents or disrupts an interaction between IGFBP and vitronectin wherein the protein complex comprises IGF-I.

The agent may be an antagonist of an interaction between an IGFBP and vitronectin or between an IGFBP-related protein and vitronectin, for example.

An example of an agent that inhibits formation of IGFBP and vitronectin complexes is IGF-II.

As will be described in more detail hereinafter, disruption of interactions between vitronectin and IGFBPs may not only inhibit tumour cell proliferation, but also inhibit tumour metastasis, both events being central to tumour pathology.

Further aspects of the invention provide uses of the isolated protein complexes and methods according to the aforementioned aspects of the invention in therapeutic or prophylactic treatments of diseases involving epithelial cells such as psoriasis, atherosclerosis, deterioration of the gastrointestinal epithelium and epithelial breast cancer, and/or in treatments which promote wound healing, skin repair, ulcer and burn healing, in vitro skin regeneration such as for grafting of autologous skin, bone regeneration and repair of damaged neuronal tissue.

Accordingly, the invention also provides a surgical implant or prosthesis comprising an isolated protein complex of the invention. The surgical implant or prosthesis may be coated, impregnated or otherwise pretreated with said isolated protein complex.

The animal treated according to the invention may be a mammal, preferably a human, or may be a non-mammalian vertebrate such as a fish, reptile or bird, or cells isolated from any of these.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE FIGURES AND TABLES

TABLE 1: List of references disclosing nucleic acids encoding growth factors and growth factor binding proteins.

TABLE 2: IGF-I and IGFBP-5 bound to vitronectin stimulates protein synthesis in HaCAT human keratinocytes. Data are derived from measurements of $^3$H-leucine incorporation and are expressed as % stimulation above control (without IGF-I, IGFBP-5 or vitronectin) over 24 hr from a single experiment in which each treatment was tested in triplicate. IGF-I was added to IGFBP-5 (5 ng/well) in the presence (+) of vitronectin (300 ng/well) or in the absence (−) of vitronectin.

FIG. 1: Competition binding assay using increasing concentrations of either insulin (▲) or (♦) to compete with [$^{125}$I]-IGF-II for binding to 300 ng vitronectin (VN) per well. Radiolabeled IGF-II (10,000 cpm) was added to VN-coated wells and the number of counts bound was determined after overnight incubation and several washes. The binding is expressed as a percentage of the binding observed in control wells with no IGF-II or insulin added. The results are shown as the average of three replicates±standard deviation from a representative of three experiments.

Figure 2:
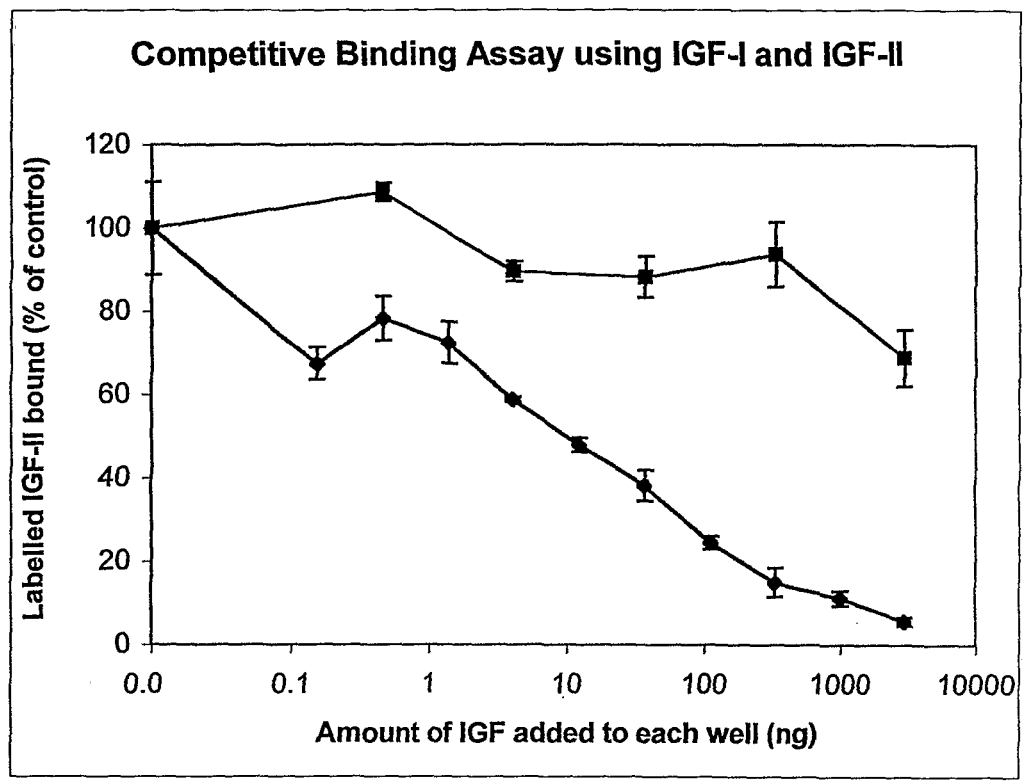

FIG. 2: Competition binding assay using increasing concentrations of either IGF-I or IGF-II to compete with [$^{125}$I]-IGF-II for binding to 300 ng vitronectin (VN) per well. Radiolabeled (10,000 cpm) was added to either VN (■)- or IGFBP2 (♦)-coated wells and the number of counts bound was determined after overnight incubation and several washes. The binding is expressed as a percentage of the binding observed in control wells with no IGF added.

Figure 3:
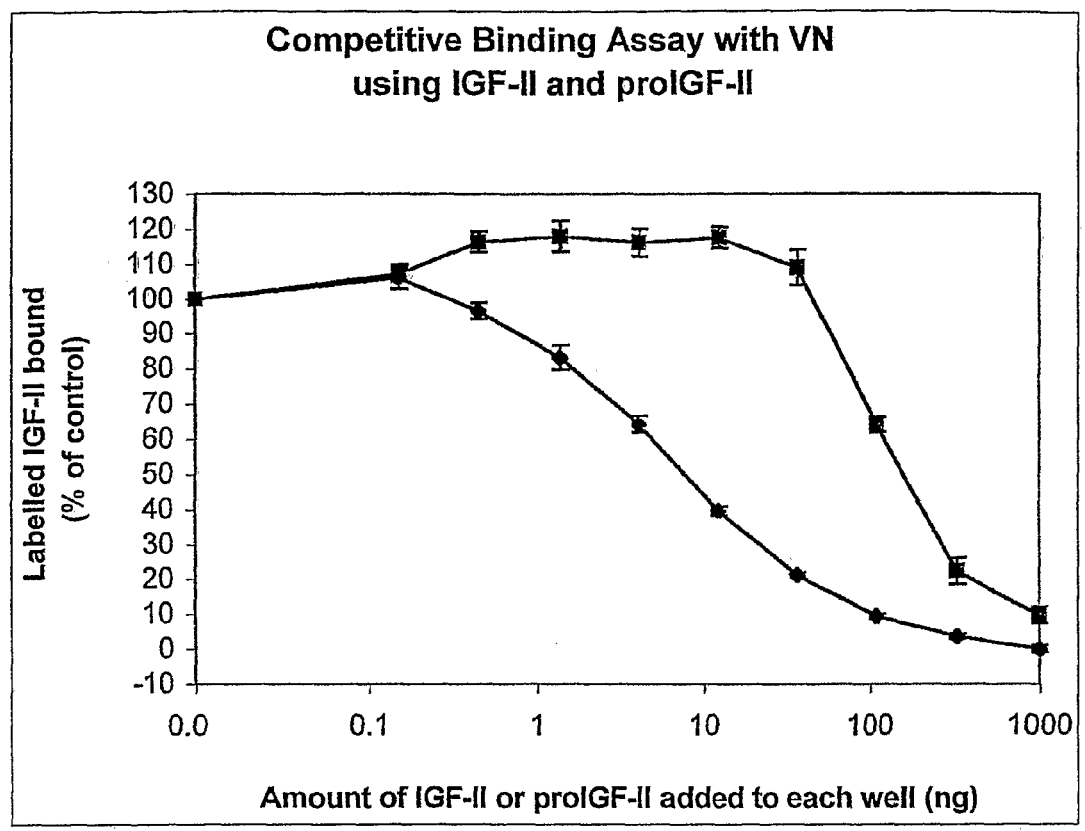

FIG. 3: Competition binding assay using increasing concentrations of either proIGF-II (■) or IGF-II (♦) to compete with [$^{125}$I]-IGF-II for binding to 300 ng vitronectin (VN) per well. Radiolabeled IGF-II (10,000 cpm) was added to vitronectin-coated wells and the number of counts bound determined after an overnight incubation and several washes. The binding is expressed as a percentage of the binding observed in the control wells with no added IGF-II or proIGF-II. The results are shown as the average of three replicates±SEM from two separate experiments.

Figure 4:
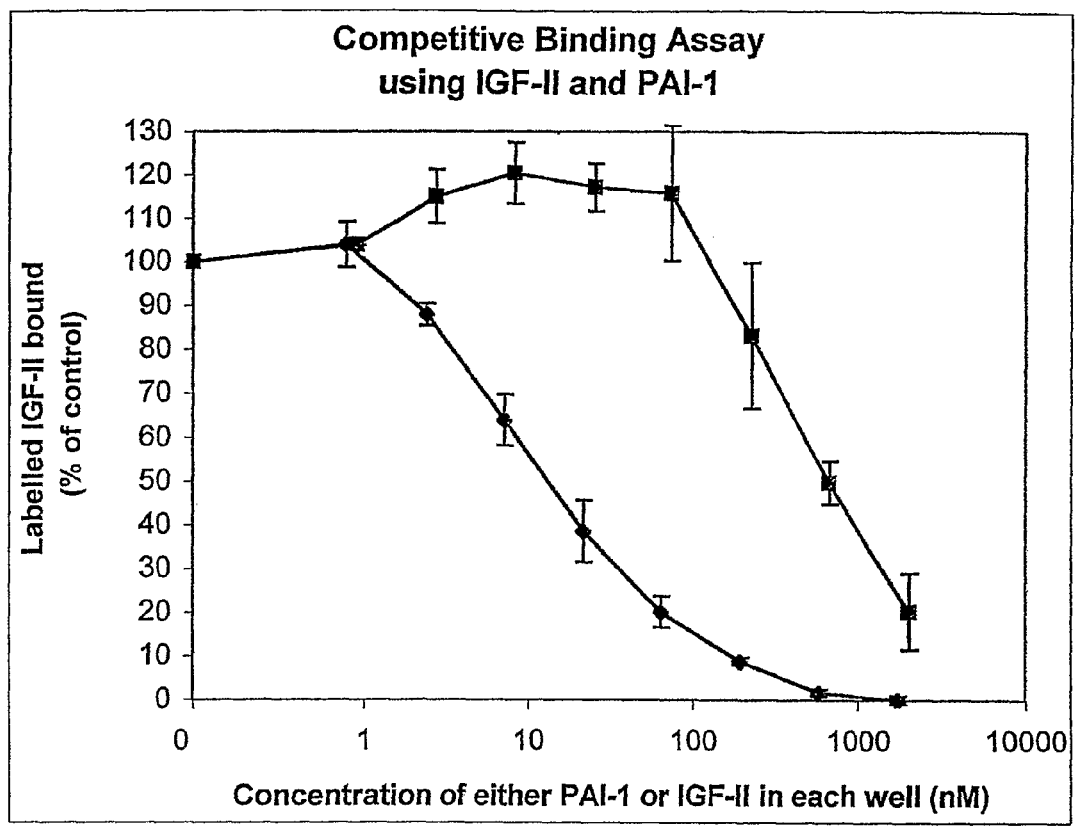

FIG. 4: Competition binding assay using increasing concentrations of either PAI-1 (■) or (♦) to compete with [$^{125}$I]-IGF-II for binding to 300 ng of vitronectin (VN) per well. Radiolabeled IGF-II (10,000 cpm) was added to vitronectin-coated well and the number of counts bound was determined after an overnight incubation and several washes. The binding is expressed as a percentage of the binding observed in the control wells with no added or IGF-II or PAI-1. The results are shown as the average of three replicates±standard deviation from a representative of three separate experiments.

Figure 5:
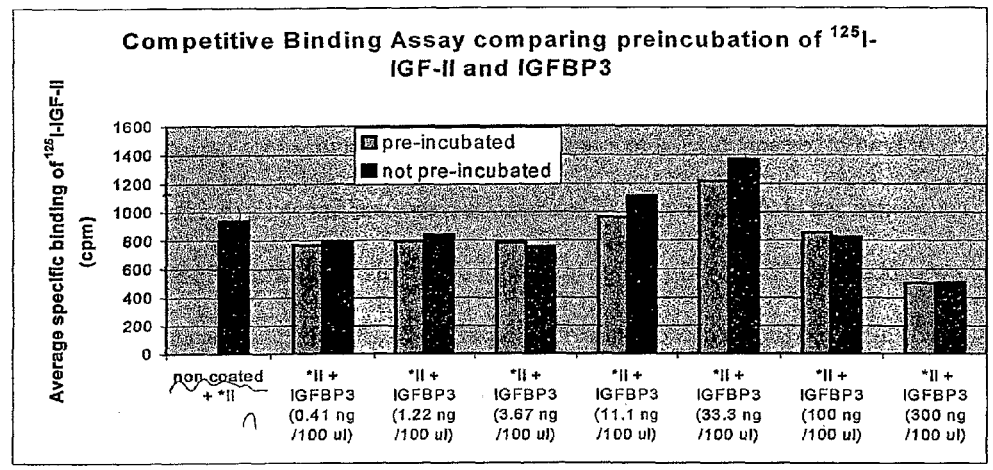
Figure 5:
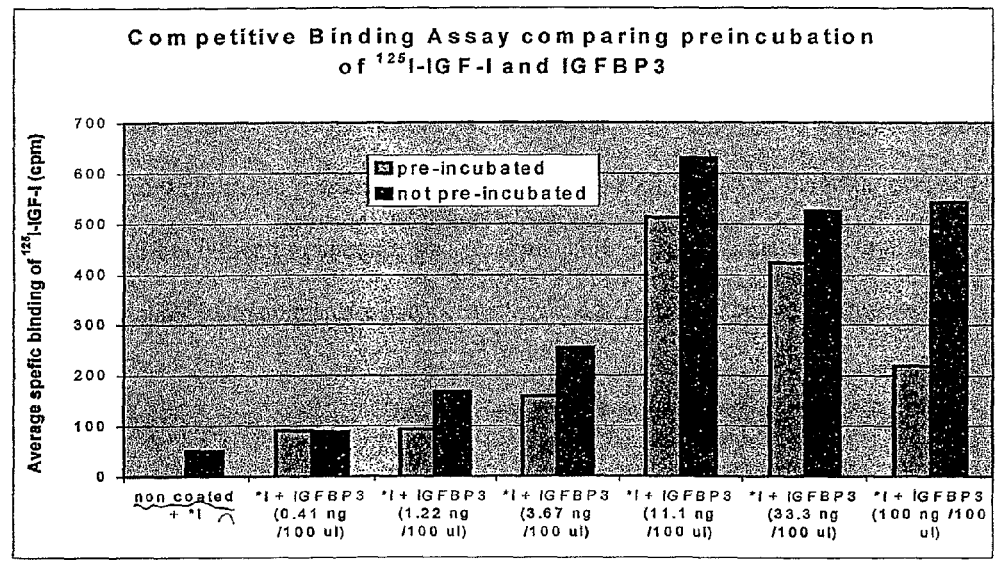

FIG. 5: Competition binding assay comparing effect of preincubation of (A) IGF-II and IGFBP3 and (B) IGF-I and IGFBP3 upon binding to vitronectin. IGFBP3 was non-glycosylated and produced in *E. coli*. Increasing concentrations of IGFBP3 plus either 10,000 cpm [$^{125}$I]-IGF-II (A) or [$^{125}$I]-IGF-I (B) were preincubated for 4 hr and added to vitronectin-coated wells. Alternatively, IGFBP3 plus either 10,000 cpm [$^{125}$I]-IGF-II (A) or [$^{125}$I]-IGF-I (B) were added to vitronectin-coated wells without preincubation. The binding is expressed as the cpm obtained in the absence of non-specific binding. The results are shown as the average of three replicates from a representative of three separate experiments.

Figure 6:
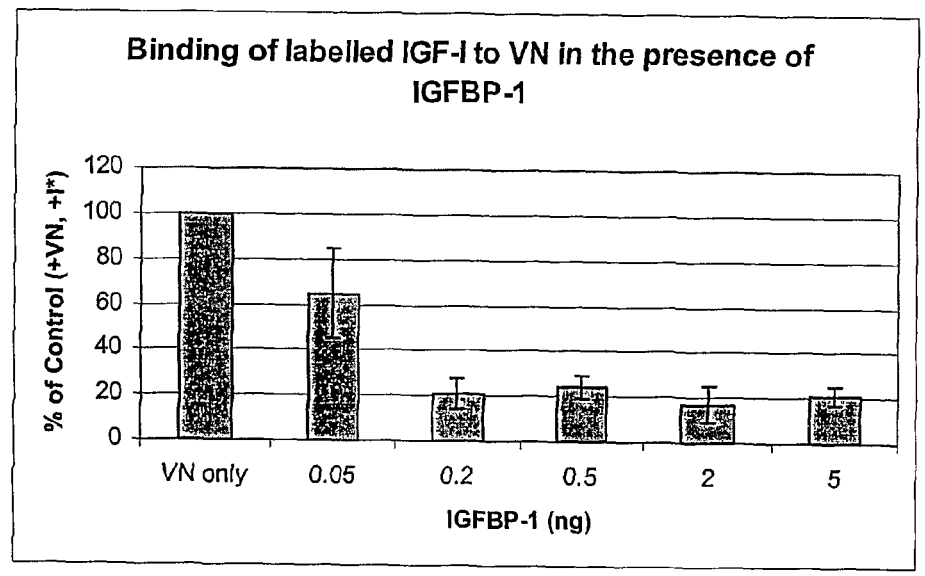
Figure 6:
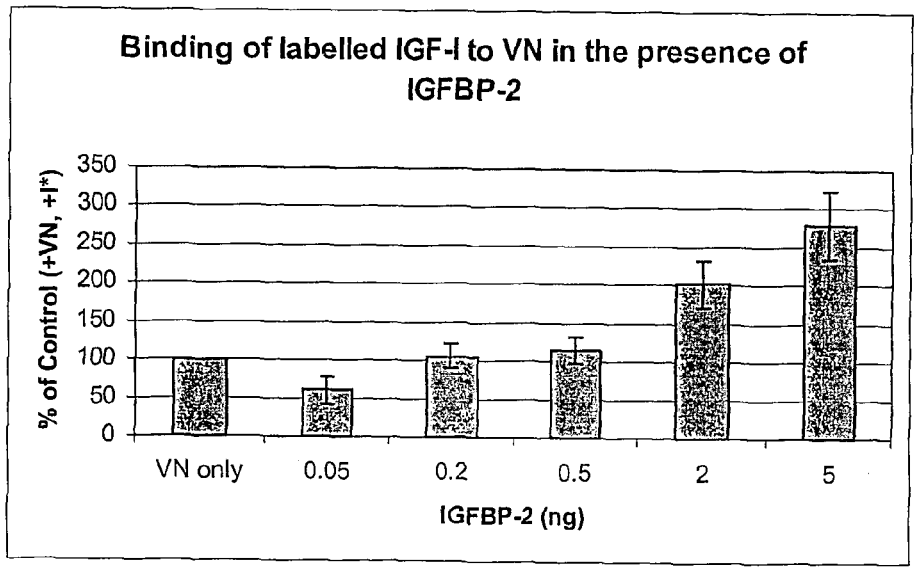
Figure 6:
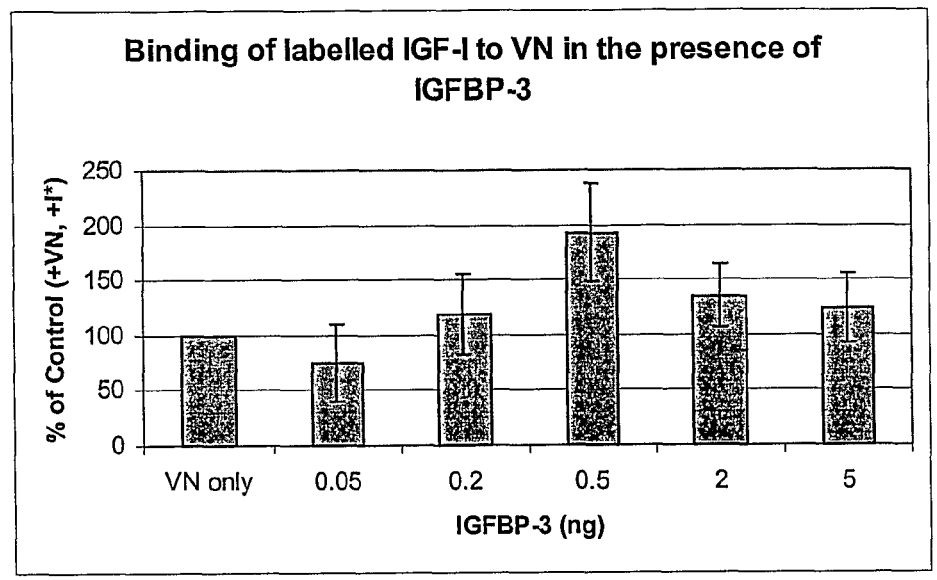
Figure 6:
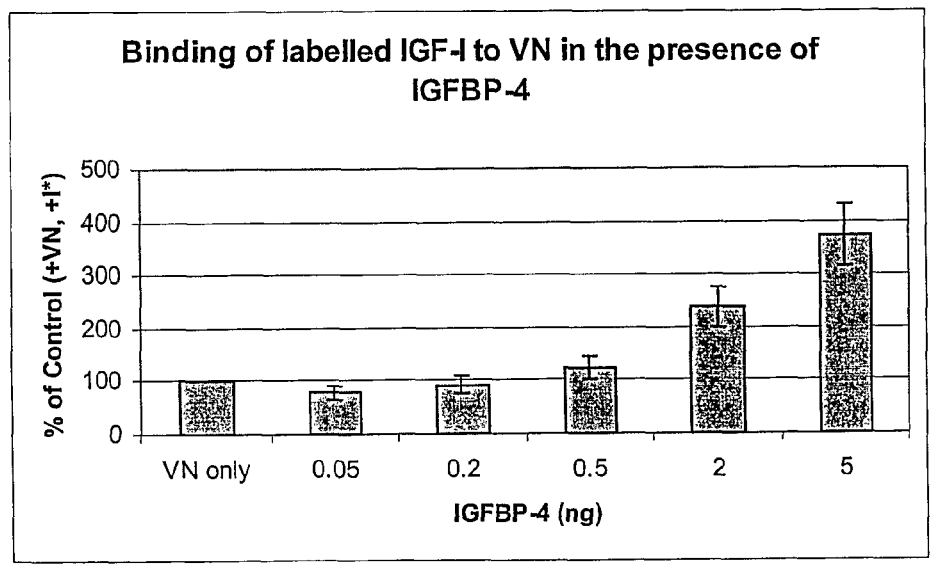
Figure 6:
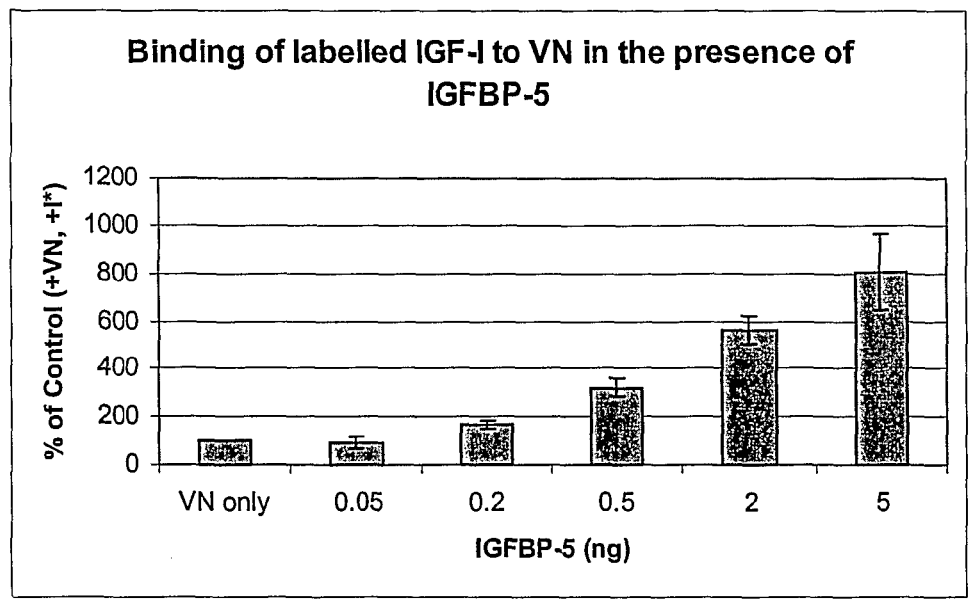
Figure 6:
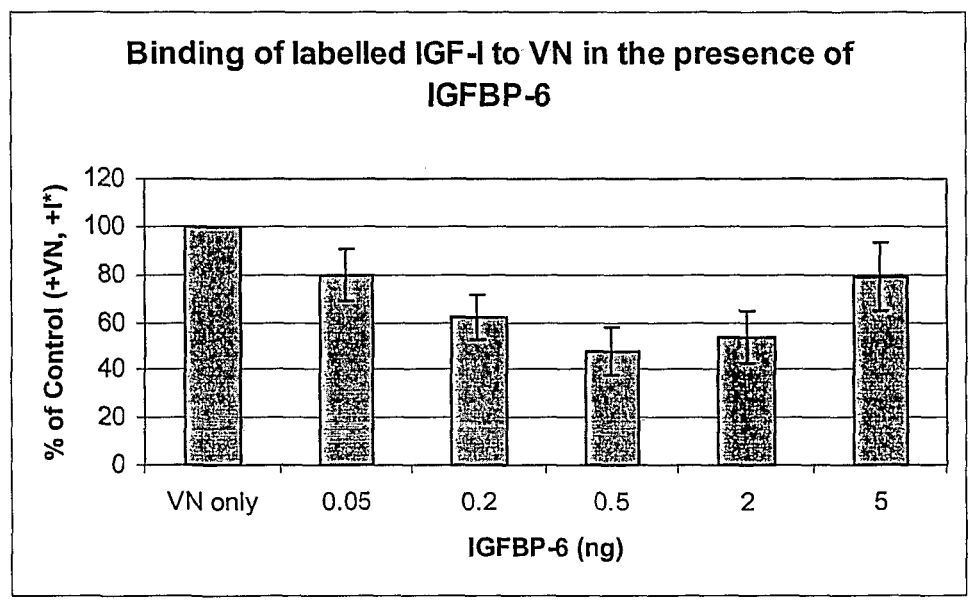

FIG. 6: Binding of labelled IGF-I to VN-coated wells in the presence of: (A) IGFBP1, (B) IGFBP2, (C) IGFBP3, (D) IGFBP4, (E) IGFBP5 and (F) IGFBP6. The recombinant IGFBPs were produced in mammalian cells. The data, expressed as average cpm of labelled IGF-I bound/VN-coated well (300 ng/well) in the presence of the indicated IGFBP are from six individual determinations. Ten thousand cpm of radiolabelled IGF-I was added to each well.

Figure 7:
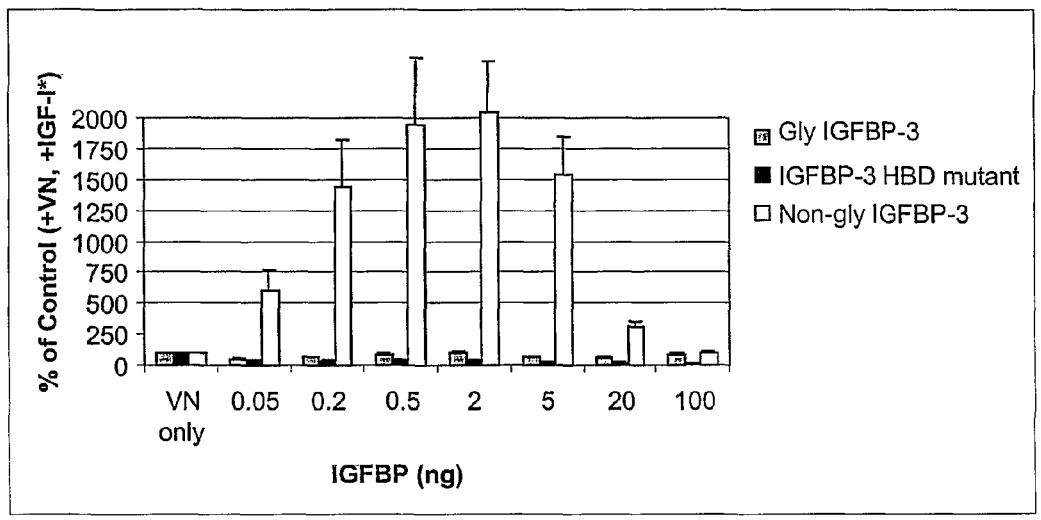

FIG. 7: Binding of labelled IGF-I to VN in the presence of "Gly IGFBP-3" (glycoslyated IGFBP-3), "IGFBP-3 HBD mutant" (IGFBP-3 with the putative heparin binding domain mutated) and to "non-gly IGFBP-3" (non-glycosylated IGFBP-3).

Figure 8:
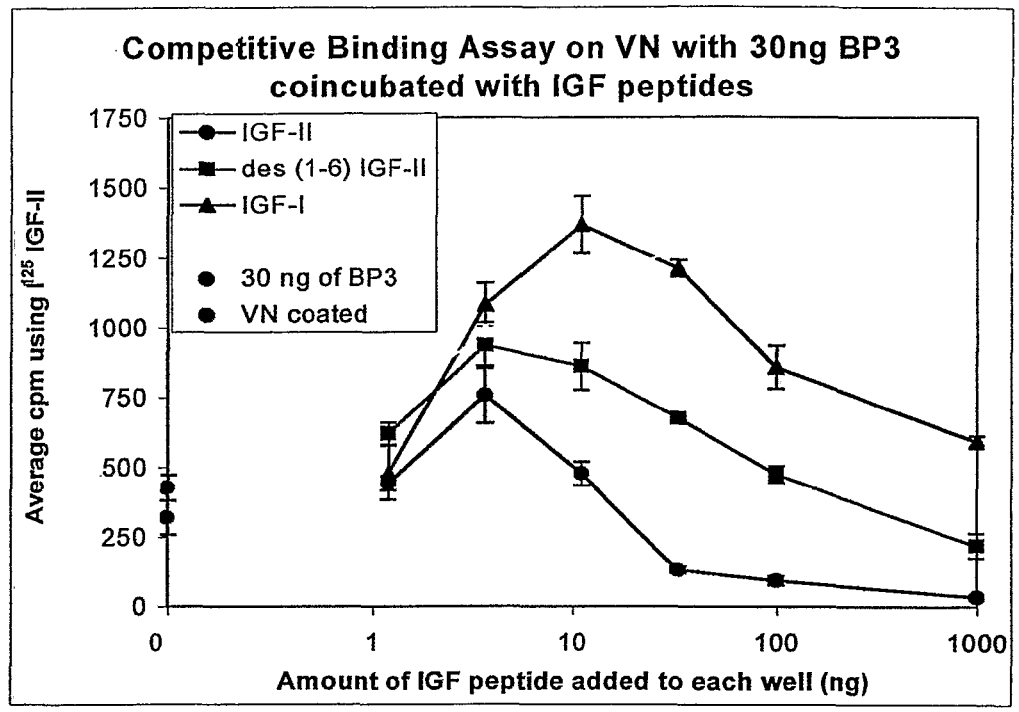
Figure 8:
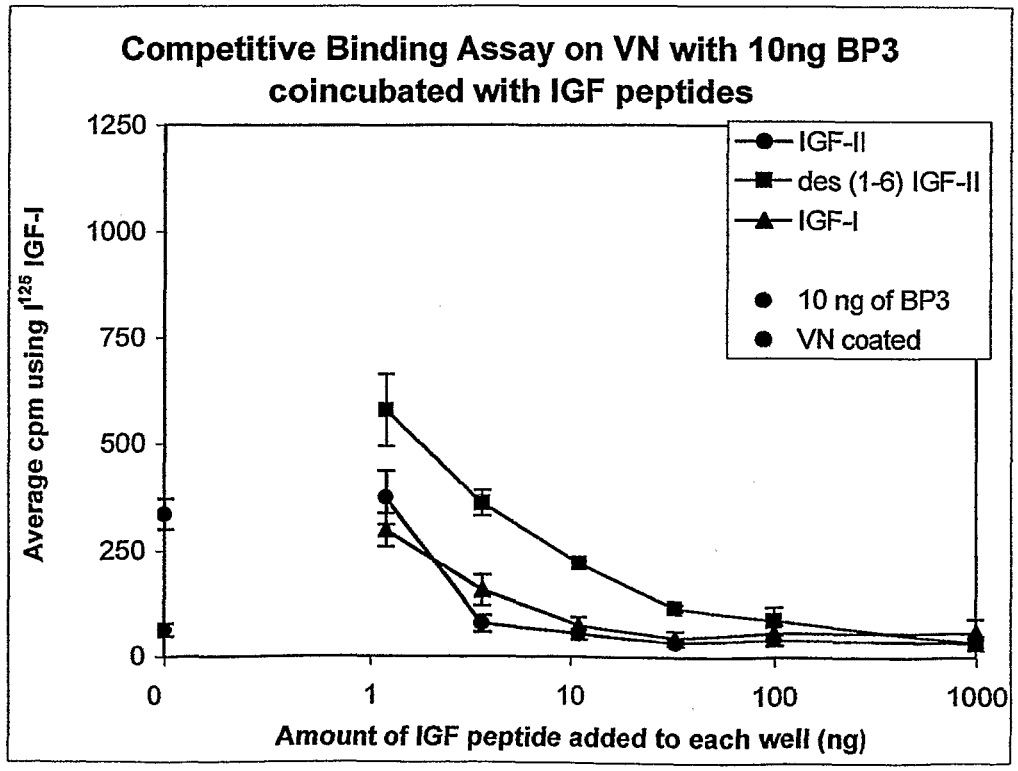

FIG. 8: Competition binding assay using increasing concentrations of IGFs and desIGFs to compete with non-glycosylated IGFBP3 incubated with [$^{125}$I]-IGF-I or -II. 30 ng (A) or 10 ng (B) of IGFBP3 plus 10,000 cpm [$^{125}$I]-IGF-II (A) or IGF-I (B) were added to VN-coated wells. Increasing concentrations of IGF-I, IGF-II, des (1-3) IGF-I (not shown) and des(1-6) IGF-II were added to compete with the radiolabel for binding to VN. Control wells coated with VN were treated with either 10 ng (A) or 30 ng (B) IGFBP3 are shown together with control wells coated with VN alone. The binding is expressed as cpm obtained in the absence of non-specific binding. The results are expressed as the average of three replicates±standard deviation from a representative of three separate experiments.

Figure 9:
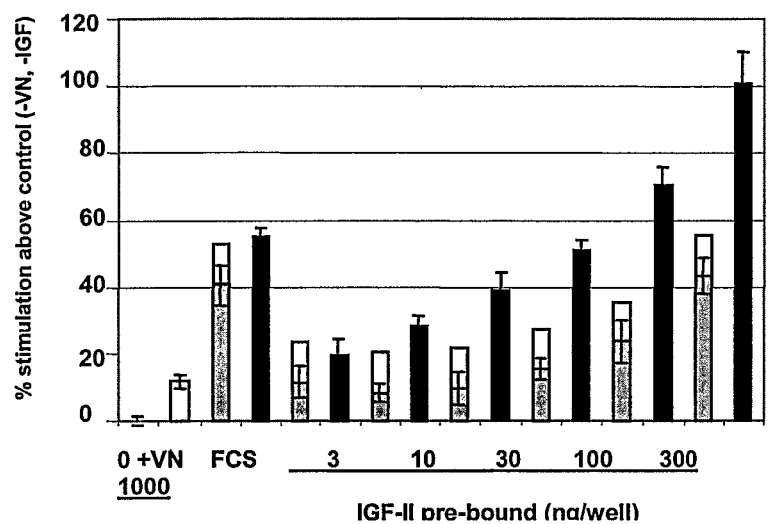

FIG. 9: Stimulation of protein synthesis in human keratinocytes. The data, expressed as % stimulation above control (-VN, -IGF-II) over 24 h is pooled from three replicate experiments in which each treatment was tested in triplicate. The theoretical additive effect represented by open bars (effect of VN alone) combined with grey bars (effect of IGF-II alone) is compared with the actual observed effect of IGF-II prebound to VN (black bars). In all instances except the lowest concentration of IGF-II tested, the actual observed effect is significantly greater (p<0.05) than the calculated additive effect.

Figure 10:
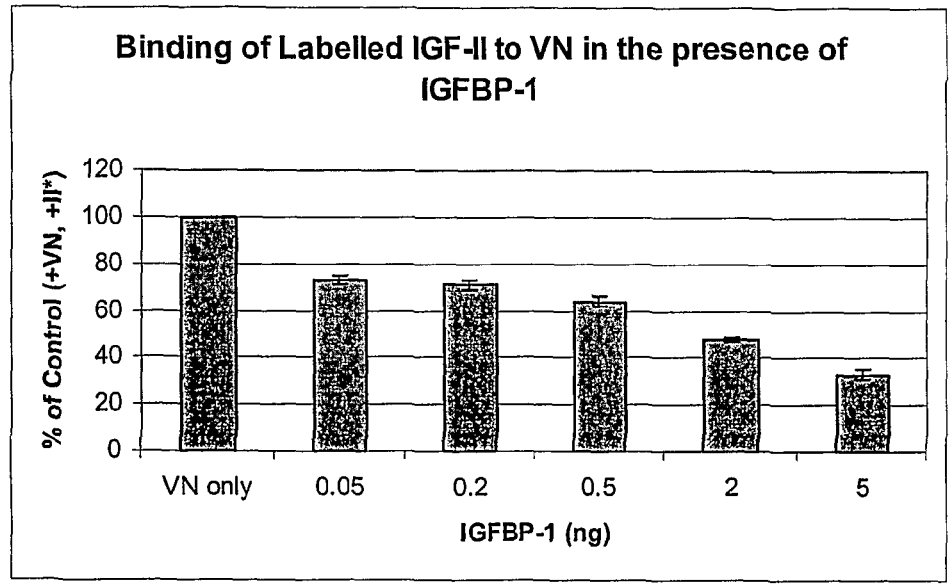
Figure 10:
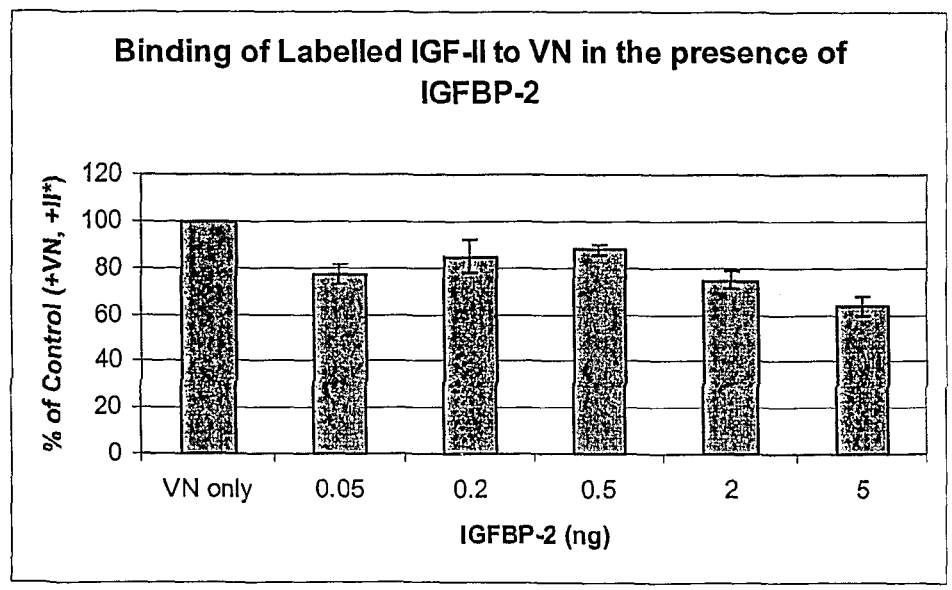
Figure 10:
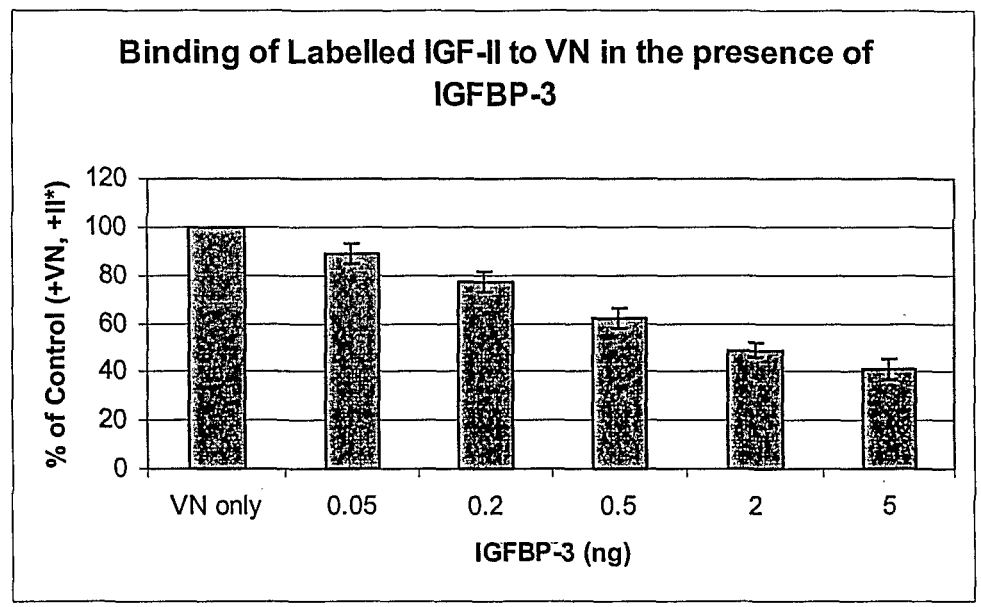
Figure 10:
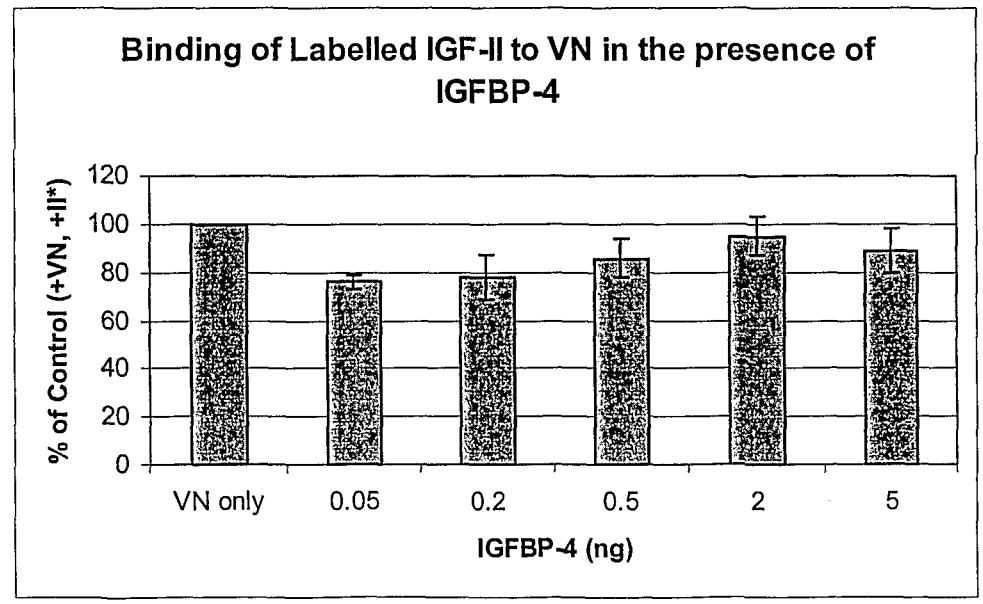
Figure 10:
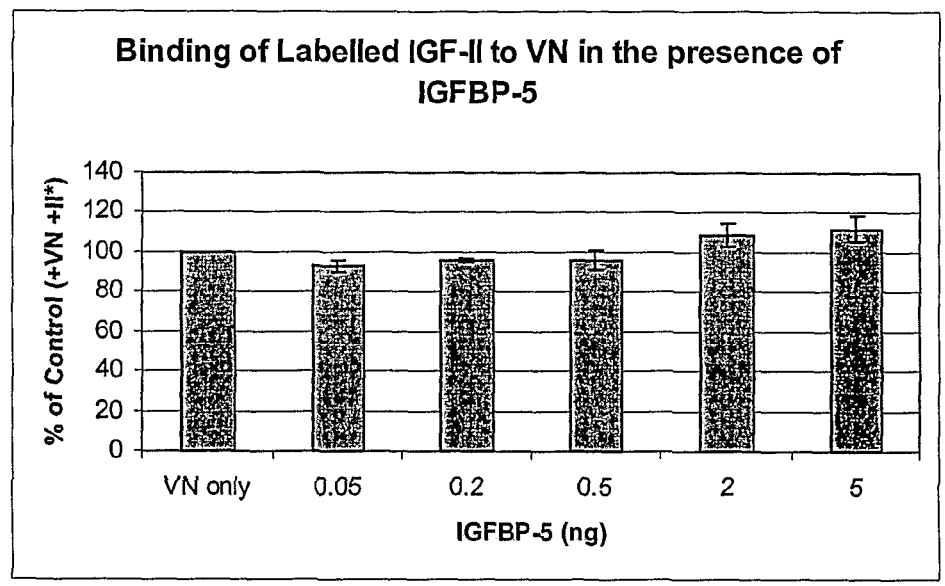
Figure 10:
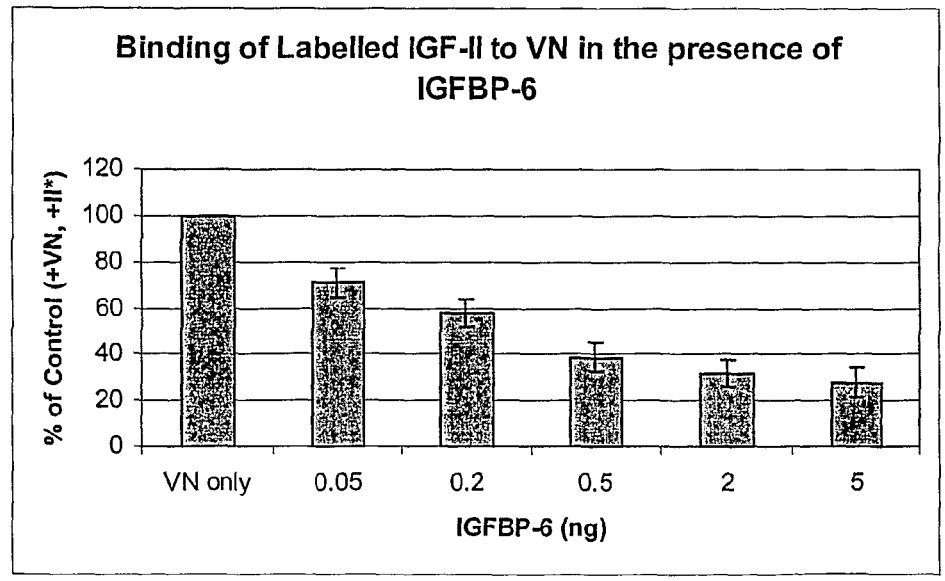

FIG. 10: Binding of labelled IGF-II to VN-coated wells in the presence of (A) IGFBP1, (B) IGFBP2, (C) IGFBP3, (D) IGFBP4, (E) IGFBP5 and (F) IGFBP6. The recombinant IGFBPs were produced in mammalian cells. The data, expressed as average cpm of labelled IGF-II bound/VN-coated well (300 ng/well) in the presence of the indicated IGFBP are from six individual determinations. Ten thousand cpm of radiolabelled IGF-II was added to each well.

DETAILED DESCRIPTION OF THE INVENTION

The present invention has arisen, at least in part, from the discovery by the present inventors that IGF-I binds vitronectin via a binding interaction between an IGFBP and vitronectin. Furthermore, the present invention describes variant IGFs and IGFBPs that may be used to augment or diminish binding between IGFS, IGFBPs and vitronectin. These discoveries have led the present inventors to manipulate these binding interactions in vitro with a view to manipulating contingent in vivo biological events associated with cell growth, proliferation and migration. This invention therefore has utility in medical treatments such as wound healing, skin repair and maintenance, bone regeneration, atherosclerosis and cancer therapy in both medical and veterinary areas.

For the purposes of this invention, by "isolated" is meant removed from a natural state or otherwise subjected to human manipulation. Isolated material may be substantially or essentially free from components that normally accompany it in its natural state, or may be manipulated so as to be in an artificial state together with components that normally accompany it in its natural state.

By "polypeptide" is also meant "protein", either term referring to an amino acid polymer.

Proteins and peptides inclusive of growth factor, growth factor binding proteins and vitronectin proteins may be isolated in native, chemical synthetic or recombinant synthetic form.

A "peptide" is a protein having no more than fifty (50) amino acids.

A "biologically-active fragment" is a fragment, portion or segment of a protein which displays at least 1%, preferably at least 10%, more preferably at least 25% and even more preferably at least 50% of the biological activity of the protein.

Peptides may be readily synthesized by recombinant or chemical synthesis techniques. For example, reference may be made to solution synthesis or solid phase synthesis as described, for example, in Chapter 9 entitled "*Peptide Synthesis*" by Atherton and Shephard which is included in a publication entitled "*Synthetic Vaccines*" edited by Nicholson and published by Blackwell Scientific Publications. Peptide synthesis methods are also described in Chapter 18 of CURRENT PROTOCOLS IN PROTEIN SCIENCE Eds. Coligan et al. (John Wiley & Sons NY, 1997) which is incorporated herein by reference. Alternatively, peptides can be produced by digestion of a polypeptide of the invention with proteinases such as endoLys-C, endoArg-C, endoGlu-C and *staphylococcus* V8-protease. The digested fragments can be purified by, for example, high performance liquid chromatographic (HPLC) techniques.

In a preferred form, the invention provides an isolated protein complex comprising vitronectin, a growth factor and a growth factor binding protein.

By "growth factor" is meant a molecule that stimulates or promotes growth of an organism or cells of said organism. A preferred growth factor is a protein or peptide that stimulates cell division, and in particular, mammalian cell division.

Preferably, isolated protein complexes of the invention comprise the growth factor IGF-I.

Isolated IGF and IGFBP polypeptides are commercially available from sources such as GroPep (Adelaide, Australia), while VN polypeptides are commercially available from sources such as Promega Corporation (Madison Wis. USA). Recombinant IGFs, IGFBPs and VN are readily made by persons skilled in the art, as will be discussed in more detail hereinafter.

As will be appreciated by the skilled person, the invention also includes precursor forms of IGFs. Examples of pro-IGF-I proteins are IGF-I proteins that have had the signal peptide removed but are not fully processed by cleavage of the E-domain. IGF-I has three different E domains that result from differential mRNA splicing and these precursor proteins may be present in isolated protein complexes of the invention.

However, the invention also contemplates isolated protein complexes comprising a growth factor such as epidermal growth factor (EGF; (Heldin et al., 1981, Science 4 1122-1123), fibroblast growth factor (FGF; Nurcombe et al., 2000, J. Biol. Chem. 275 30009-30018), basic fibroblast growth factor (bFGF; Taraboletti et al., 1997, Cell Growth. Differ. 8 471-479), osteopontin (Nam et al., 2000, Endocrinol. 141 1100), thrombospondin-1 (Nam et al., 2000, supra), tenascin-C (Arai et al., 1996, J. Biol. Chem. 271 6099), PAI-1 (Nam et al., 1997, Endocrinol. 138 2972), plasminogen (Campbell et al., 1998, Am. J. Physiol. 275 E321), fibrinogen (Campbell et al., 1999, J. Biol. Chem. 274 30215), fibrin (Campbell et al., 1999, supra) or transferrin (Weinzimer et al., 2001, J. Clin. Endocrinol. Metab. 86 1806).

Preferably, isolated protein complexes comprising osteopontin thrombospondin-1, tenascin-C or PAI-1 further comprise IGFBP-5.

Preferably, isolated protein complexes comprising plasminogen fibrinogen, fibrin or transferrin further comprise IGFBP-3.

The invention contemplates isolated protein complexes comprising monomeric and multimeric vitronectin, as vitronectin can exist in monomeric and multimeric states. In particular, multimeric VN accumulates in areas of vascular injury and also is the predominant form of VN in tissue. Thus the multimeric form of VN provides the opportunity to form a VN complex in which more than one type of growth factor or growth factor binding protein can be delivered at the same time.

It will also be appreciated by the skilled person that isolated protein complexes of the invention may include vitronectin in "native", "denatured" or "extended" states as are well understood in the art.

The invention also contemplates isolated growth factor complexes comprising nectinepsin, which is an extracellular matrix protein that shows 60% homology to VN at the amino acid level (Blanchert et al., 1996, J. Biol. Chem. 271 26220-26226).

It will also be understood that variants of growth factors, growth factor binding proteins and/or vitronectin may be used to form isolated protein complexes of the invention and may be useful in the methods of use set forth herein.

As used herein, "variant" proteins, polypeptides and peptides of the invention include those in which one or more amino acids have been replaced by different amino acids.

It is well understood in the art that some amino acids may be changed to others with broadly similar properties without changing the nature of the activity of the polypeptide (conservative substitutions).

Substantial changes in function may be made by selecting substitutions that are less conservative. Other replacements would be non-conservative substitutions and relatively fewer of these may be tolerated. Generally, the substitutions which are likely to produce the greatest changes in a polypeptide's properties are those in which (a) a hydrophilic residue (e.g., Ser or Thr) is substituted for, or by, a hydrophobic residue (e.g., Ala, Leu, Ile, Phe or Val); (b) a cysteine or proline is substituted for, or by, any other residue; (c) a residue having an electropositive side chain (e.g., Arg, His or Lys) is substituted for, or by, an electronegative residue (e.g., Glu or Asp) or (d) a residue having a bulky side chain (e.g., Phe or Trp) is substituted for, or by, one having a smaller side chain (e.g., Ala, Ser) or no side chain (e.g., Gly).

Variants also include proteins, polypeptides and peptides which have been altered, for example by conjugation or complexing with other chemical moieties or by post-translational modification techniques as would be understood in the art. Such derivatives include amino acid deletions and/or additions.

Other polypeptide and peptide variants contemplated by the invention include, but are not limited to, modification to side chains, incorporation of unnatural amino acids and/or their derivatives during peptide, polypeptide or protein synthesis and the use of crosslinkers and other chemicals which impose conformational constraints on the polypeptides and peptide variants of the invention. Examples of side chain modifications contemplated by the present invention include modifications of amino groups such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with $NaBH_4$; reductive alkylation by reaction with an aldehyde followed by reduction with $NaBH_4$; and trinitrobenzylation of amino groups with 2, 4, 6-trinitrobenzene sulphonic acid (TNBS).

The carboxyl group may be modified by carbodiimide activation via O-acylisourea formation followed by subsequent derivitization, by way of example, to a corresponding amide.

The guanidine group of arginine residues may be modified by formation of heterocyclic condensation products with reagents such as 2,3-butanedione, phenylglyoxal and glyoxal.

Sulphydryl groups may be modified by methods such as performic acid oxidation to cysteic acid; formation of mercurial derivatives using 4-chloromercuriphenylsulphonic acid, 4-chloromercuribenzoate; 2-chloromercuri-4-nitrophenol, phenylmercury chloride, and other mercurials; formation of a mixed disulphides with other thiol compounds; reaction with maleimide, maleic anhydride or other substituted maleimide; carboxymethylation with iodoacetic acid or iodoacetamide; and carbamoylation with cyanate at alkaline pH.

Tryptophan residues may be modified, for example, by alkylation of the indole ring with 2-hydroxy-5-nitrobenzyl bromide or sulphonyl halides or by oxidation with N-bromosuccinimide.

Tyrosine residues may be modified by nitration with tetranitromethane to form a 3-nitrotyrosine derivative.

The imidazole ring of a histidine residue may be modified by N-carbethoxylation with diethylpyrocarbonate or by alkylation with iodoacetic acid derivatives.

Examples of incorporating unnatural amino acids and derivatives during peptide synthesis include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids.

Modifications also include within their scope O- and N-linked glycosylation variants and non-glycosylated forms of proteins that, in their naturally-occurring state, are glycosylated.

With regard to variants, these may be created by mutagenizing a polypeptide or by mutagenizing an encoding nucleic acid, such as by random mutagenesis or site-directed mutagenesis. Examples of nucleic acid mutagenesis methods are provided in Chapter 9 of CURRENT PROTOCOLS IN MOLECULAR BIOLOGY, Ausubel et al., supra which is incorporated herein by reference.

It will be appreciated by the skilled person that site-directed mutagenesis is best performed where knowledge of the amino acid residues that contribute to biological activity is available. In many cases, this information is not available, or can only be inferred by molecular modelling approximations, for example.

In such cases, random mutagenesis is contemplated. Random mutagenesis methods include chemical modification of proteins by hydroxylamine (Ruan et al., 1997, Gene 188 35), incorporation of dNTP analogs into nucleic acids (Zaccolo et al., 1996, J. Mol. Biol. 255 589) and PCR-based random mutagenesis such as described in Stemmer, 1994, Proc. Natl. Acad. Sci. USA 91 10747 or Shafikhani et al., 1997, Biotechniques 23 304, each of which references is incorporated herein. It is also noted that PCR-based random mutagenesis kits are commercially available, such as the Diversify™ kit (Clontech).

The invention also contemplates use of growth factor variants such as des(1-6)IGF-II and des(1-3)IGF-I to form isolated protein complexes of the invention.

Other variant IGFs and IGFBPs useful as agonists or antagonists will be described in more detail hereinafter.

Recombinant Growth Factor Complexes

It will be appreciated that isolated protein complexes may be produced using recombinant growth factors, growth factor binding proteins and/or vitronectin, by expression of an encoding nucleic acid in an appropriate host cell or in a cell-free expression system as are well known in the art.

The term "nucleic acid" as used herein designates single- or double-stranded mRNA, RNA, cRNA and DNA, said DNA inclusive of cDNA and genomic DNA.

A "polynucleotide" is a nucleic acid having eighty (80) or more contiguous nucleotides, while an "oligonucleotide" has less than eighty (80) contiguous nucleotides.

A "probe" may be a single or double-stranded oligonucleotide or polynucleotide, suitably labeled for the purpose of detecting complementary sequences in Northern or Southern blotting, for example.

A "primer" is usually a single-stranded oligonucleotide, preferably having 15-50 contiguous nucleotides, which is capable of annealing to a complementary nucleic acid "template" and being extended in a template-dependent fashion by the action of a DNA polymerase such as Taq polymerase, RNA-dependent DNA polymerase or Sequenase™.

Nucleic acids encoding IGFs, EGF, IGFBPs, ALS and VN are well known in the art and have been available for many years. However, the skilled person is referred to Table 1 which lists references that provide examples of these nucleic acid sequences. All references in Table 1 are incorporated herein by reference.

Nucleic acids useful according to the present invention may be prepared according to the following procedure:
(i) creating primers which are, optionally, degenerate wherein each comprises a respective portion of a target nucleic acid; and
(ii) using said primers in combination with a nucleic acid amplification technique to amplify one or more amplification products from a nucleic acid extract.

Suitable nucleic acid amplification techniques are well known to the skilled person, and include polymerase chain reaction (PCR) as for example described in Chapter 15 of Ausubel et al. supra, which is incorporated herein by reference; strand displacement amplification (SDA) as for example described in U.S. Pat. No. 5,422,252 which is incorporated herein by reference; rolling circle replication (RCR) as for example described in Liu et al., 1996, J. Am. Chem. Soc. 118 1587, International application WO 92/01813 and International Application WO 97/19193 which are incorporated herein by reference; nucleic acid sequence-based amplification (NASBA) as for example described by Sooknanan et al., 1994, Biotechniques 17 1077 which is incorporated herein by reference; ligase chain reaction (LCR) as for example described in International Application WO89/09385 which is incorporated by reference herein; and Q-β replicase amplification as for example described by Tyagi et al., 1996, Proc. Natl. Acad. Sci. USA 93 5395 which is incorporated herein by reference.

As used herein, an "amplification product" refers to a nucleic acid product generated by nucleic acid amplification techniques.

Recombinant proteins may be prepared by any suitable procedure known to those of skill in the art.

For example, the recombinant protein may be prepared by a procedure including the steps of:
(i) preparing an expression construct which comprises a nucleic acid, operably linked to one or more regulatory nucleotide sequences;
(ii) transfecting or transforming a suitable host cell with the expression construct; and
(iii) expressing the polypeptide in said host cell.

For the purposes of host cell expression, the recombinant nucleic acid is operably linked to one or more regulatory sequences in an expression vector.

An "expression vector" may be either a self-replicating extra-chromosomal vector such as a plasmid, or a vector that integrates into a host genome.

By "operably linked" is meant that said regulatory nucleotide sequence(s) is/are positioned relative to the recombinant nucleic acid of the invention to initiate, regulate or otherwise control transcription.

Regulatory nucleotide sequences will generally be appropriate for the host cell used for expression. Numerous types of appropriate expression vectors and suitable regulatory sequences are known in the art for a variety of host cells.

Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences.

Constitutive or inducible promoters as known in the art are contemplated by the invention. The promoters may be either naturally occurring promoters, or hybrid promoters that combine elements of more than one promoter.

In a preferred embodiment, the expression vector contains a selectable marker gene to allow the selection of transformed host cells. Selectable marker genes are well known in the art and will vary with the host cell used.

The expression vector may also include a fusion partner (typically provided by the expression vector) so that the recombinant polypeptide of the invention is expressed as a fusion polypeptide with said fusion partner. The main advantages of fusion partners are that they assist identification and/or purification of said fusion polypeptide and also enhance protein expression levels and overall yield.

In order to express said fusion polypeptide, it is necessary to ligate a nucleotide sequence according to the invention into the expression vector so that the translational reading frames of the fusion partner and the nucleotide sequence of the invention coincide.

Well known examples of fusion partners include, but are not limited to, glutathione-S-transferase (GST), Fc potion of human IgG, maltose binding protein (MBP) and hexahistidine ($HIS_6$), which are particularly useful for isolation of the fusion polypeptide by affinity chromatography. For the purposes of fusion polypeptide purification by affinity chromatography, relevant matrices for affinity chromatography are glutathione-, amylose-, and nickel- or cobalt-conjugated resins respectively. Many such matrices are available in "kit" form, such as the QIAexpress™ system (Qiagen) useful with ($HIS_6$) fusion partners and the Pharmacia GST purification system.

Another fusion partner well known in the art is green fluorescent protein (GFP). This fusion partner serves as a fluorescent "tag" which allows the fusion polypeptide of the invention to be identified by fluorescence microscopy or by flow cytometry. The GFP tag is useful when assessing subcellular localization of the fusion polypeptide of the invention, or for isolating cells which express the fusion polypeptide of the invention. Flow cytometric methods such as fluorescence activated cell sorting (FACS) are particularly useful in this latter application.

In some cases, the fusion partners also have a protease cleavage site, such as for Factor $X_a$ or Thrombin, which allow the relevant protease to partially digest the fusion polypeptide of the invention and thereby liberate the recombinant polypeptide of the invention therefrom. The liberated polypeptide can then be isolated from the fusion partner by subsequent chromatographic separation.

Fusion partners according to the invention also include within their scope "epitope tags", which are usually short peptide sequences for which a specific antibody is available. Well known examples of epitope tags for which specific monoclonal antibodies are readily available include c-myc, influenza virus haemagglutinin and FLAG tags.

The recombinant protein may be conveniently prepared by a person skilled in the art using standard protocols as for example described in Sambrook, et al., MOLECULAR CLONING. A Laboratory Manual (Cold Spring Harbor Press, 1989), incorporated herein by reference, in particular Chapter 16 and 17; CURRENT PROTOCOLS IN MOLECULAR BIOLOGY Eds. Ausubel et al., (John Wiley & Sons, Inc. 1995-1999), incorporated herein by reference, in particular Chapters 10 and 16; and CURRENT PROTOCOLS IN PROTEIN SCIENCE Eds. Coligan et al., (John Wiley & Sons, Inc. 1995-1999) which is incorporated by reference herein, in particular Chapters 1, 5 and 6.

In one embodiment, recombinant expression of growth factor, growth factor binding protein and vitronectin may be performed separately, and complexes formed therefrom.

In another embodiment, recombinant expression of growth factor, growth factor binding protein and vitronectin may be performed in the same cell, and complexes formed therefrom.

As hereinbefore, polypeptides of the invention may be produced by culturing a host cell transformed with said expression construct comprising a nucleic acid encoding a polypeptide, or polypeptide homolog, of the invention. The conditions appropriate for protein expression will vary with the choice of expression vector and the host cell. This is easily ascertained by one skilled in the art through routine experimentation.

Suitable host cells for recombinant expression include bacteria such as *E. coli, Clostridium* sp., *Pseudomonas* sp., yeast, plant cells, insect cells (such as Sf9) and mammalian cells such as fibroblasts and keratinocytes.

Preferred host cells are human keratinocytes.

Inducible and non-inducible expression vectors are contemplated. In stably transfected mammalian cells, a number of inducible and repressible systems have been devised including metallothionine (MT) inducible and tetracycline and repressible (tetR), each of which is contemplated by the present invention.

Particular examples of suitable expression vectors and methods of recombinant IGFBP expression may be found in U.S. Pat. No. 5,973,115 which is incorporated herein by reference.

Mimetics, Agonists and Antagonists

The invention contemplates agents which may promote, prevent or disrupt formation of protein complexes comprising growth factors, growth factor binding proteins and vitronectin. Such an agent may be a mimetic. The term "mimetic" is used herein to refer to molecules that are designed to resemble particular functional regions of proteins or peptides, and includes within its scope the terms "agonist", "analogue" and "antagonist" as are well understood in the art.

Of relevance is the elucidation of the portions of IGFs and IGFBPs which are responsible for IGF-IGFBP binding, as described in International Publication WO00/23469. Furthermore, agonist variants of IGF-I have been made which selectively bind IGFBP-1 or IGFBP-3, as described in International Publication WO00/40612.

It is therefore contemplated that agents could be engineered which disrupt or prevent formation of polypeptide complexes between IGFBPs and VN. An example would be a peptide which competes for binding of the IGFBP to VN by resembling the binding site on VN or the IGFBP.

As will be described in more detail hereinafter, IGF-II is an agent that can inhibit binding between an IGFBP and vitronectin. It is also proposed that residues $V^{35}$ or $S^{36}$ along with $S^{39}$ of the RVSRRSR (SEQ ID NO: 1) sequence at positions 34-40 in the C-domain of IGF-II could be deleted to thereby resemble the HBD of IGFBP3 (BXBBB wherein B is a basic amino acid residue); (SEQ ID NO: 2). This would create an agent even more capable of inhibiting formation of a complex between IGFBPs and vitronectin.

An example of an agonist contemplated by the present invention is IGF-1 engineered to include a heparin binding domain (HBD) of an IGFBP to thereby bind vitronectin directly. For example, the sequence SSSRRAPQT (SEQ ID NO: 3) in the C-domain of IGF-I may be engineered to have a BXBBB (SEQ ID NO: 2) motif. A preferred BXBBB (SEQ ID NO: 2) motif is the KGRKR (SEQ ID NO. 4) sequence of IGFBP-3 (residues 228-232).

Alternatively, the putative vitronectin-binding domain of IGF-II: RVSRRSR (SEQ ID NO: 1; residues 34-40) may be introduced into IGF-I.

An example of an antagonist of the invention is an IGFBP engineered to mutate basic residues in the HBD (as hereinbefore described) to reduce or prevent binding of the IGFBP to vitronectin.

Suitably, the engineered IGFBP is capable of binding IGF-I.

Preferably, the engineered IGFBP is IGFBP-3 or IGFBP-5.

It is also contemplated that an analogue of an IGFBP could be engineered which enables formation of a complex between the analogue and VN. Suitably, the analogue would also bind an IGF. Potential advantages of such an analogue is that it might be more readily synthesized or isolated than an IGFBP, have a particular desired biological half-life and perhaps be engineered to specifically bind IGF-I.

The aforementioned mimetics may be peptides, polypeptides or other organic molecules, preferably small organic molecules, with a desired biological activity and half-life.

Computer-assisted structural database searching is becoming increasingly utilized as a procedure for identifying mimetics. Database searching methods which, in principle, may be suitable for identifying mimetics, may be found in International Publication WO 94/18232 (directed to producing HIV antigen mimetics), U.S. Pat. No. 5,752,019 and International Publication WO 97/41526 (directed to identifying EPO mimetics), each of which is incorporated herein by reference.

Other methods include a variety of biophysical techniques which identify molecular interactions. These allow for the screening of candidate molecules according to whether said candidate molecule affects formation of IGF-IGFBP-VN complexes, for example. Methods applicable to potentially useful techniques such as competitive radioligand binding assays (see Upton et al., 1999, supra for a relevant method), analytical ultracentrifugation, microcalorimetry, surface plasmon resonance and optical biosensor-based methods are provided in Chapter 20 of CURRENT PROTOCOLS TN PROTEIN SCIENCE Eds. Coligan et al., (John Wiley & Sons, 1997) which is incorporated herein by reference.

Pharmaceutical Compositions

The invention includes administration of a protein complex of the invention in the form of a pharmaceutical composition. Pharmaceutical compositions of the invention may include isolated protein complexes that comprise variant IGFs and/or IGFBPs or agents that disrupt or prevent formation of said complexes as hereinbefore described.

Suitably, the pharmaceutical composition comprises a pharmaceutically-acceptable carrier. Pharmaceutical compositions may also include polypeptide variants, fragments or mimetics as hereinbefore defined.

By "pharmaceutically-acceptable carrier" is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline, and pyrogen-free water.

Any suitable route of administration may be employed for providing a patient with the composition of the invention. For example, oral, rectal, parenteral, sublingual, buccal, intravenous, intra-articular, intra-muscular, intra-dermal, subcutaneous, inhalational, intraocular, intraperitoneal, intracerebroventricular, transdermal and the like may be employed. Intra-muscular and subcutaneous injection is appropriate, for example, for administration of immunogenic compositions, vaccines and DNA vaccines.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

Pharmaceutical compositions of the present invention suitable for oral or parenteral administration may be presented as discrete units such as capsules, sachets or tablets each containing a pre-determined amount of one or more therapeutic agents of the invention, as a powder or granules or as a solution or a suspension in an aqueous liquid, a non-aqueous liquid, an oil-in-water emulsion or a water-in-oil liquid emulsion.

With regard to pharmaceutical compositions comprising IGF and IGFBPs, particular reference is made to U.S. Pat. No. 5,936,064 and International Publications WO99/62536 and WO99/54359 which are incorporated herein by reference.

Pharmaceutical compositions of the invention may also include expression vectors such as viral vectors such as vaccinia, and viral vectors useful in gene therapy. The latter include adenovirus and adenovirus-associated viruses (AAV) such as described in Braun-Falco et al., 1999, Gene Ther. 6 432, retroviral and lentiviral vectors such as described in Buchshacher et al., 2000, Blood 95 2499 and vectors derived from herpes simplex virus and cytomegalovirus. A general overview of viral vectors useful in endocrine gene therapy is provided in Stone et al., 2000, J. Endocrinol. 164 103.

The present invention may also utilize specific expression vectors which target gene expression to epidermal cells, such as described in U.S. Pat. No. 5,958,764 and for in vivo wound healing applications, such as described in U.S. Pat. No. 5,962,427.

Each of the aforementioned publications is incorporated herein by reference.

Therapeutic Uses

The invention provides methods of treatment using polypeptide complexes of the invention. These methods are particularly aimed at therapeutic treatment of mammals, and more particularly, humans.

Such methods include administration of pharmaceutical compositions as hereinbefore defined, and may be by way of microneedle injection into specific tissue sites, such as described in U.S. Pat. No. 6,090,790, topical creams, lotions or sealant dressings applied to wounds, burns or ulcers, such as described in U.S. Pat. No. 6,054,122 or implants which release the composition such as described in International Publication WO99/47070.

Gene therapy is also applicable in this regard, such as according to methods set forth in U.S. Pat. No. 5,929,040 and U.S. Pat. No. 5,962,427.

There also exist methods by which skin cells can be genetically modified for the purpose of creating skin substitutes, such as by genetically engineering desired growth factor expression (Supp et al., 2000, J. Invest. Dermatol. 114 5). An example of a review of this field is provided in Bevan et al., Biotechnol. Gent. Eng. Rev. 16 231.

Also contemplated is "seeding" a recipient with transfected or transformed cells, such as described in International Publication WO99/11789.

These methods can be used to stimulate cell proliferation and thereby facilitate or progress wound and burn healing, repair of skin lesions such as ulcers, tissue replacement and grafting such as by in vitro culturing of autologous skin, re-epithelialization of internal organs such as kidney and lung and repair of damaged nerve tissue.

Skin replacement therapy has become well known in the art, and may employ use of co-cultured epithelial/keratinocyte cell lines, for example as described in Kehe et al., 1999, Arch. Dermatol. Res. 291 600 or in vitro culture of primary (usually autologous) epidermal, dermal and/or keratinocyte cells. These techniques may also utilize engineered biomaterials and synthetic polymer "scaffolds".

Examples of reviews of the field in general are provided in Terskikh & Vasiliev, 1999, Int. Rev. Cytol. 188 41 and Eaglestein & Falanga, 1998, Cutis 62 1.

More particularly, the production of replacement oral mucosa useful in craniofacial surgery is described in Izumi et al., 2000, J. Dent. Res. 79 798. Fetal keratinocytes and dermal fibroblasts can be expanded in vitro to produce skin for grafting to treat skin lesions, such as described in Fauza et al., J. Pediatr. Surg. 33 357, while skin substitutes from dermal and epidermal skin elements cultured in vitro on hyaluronic acid-derived biomaterials have been shown to be potentially useful in the treatment of burns (Zacchi et al., 1998, J. Biomed. Mater. Res. 40 187).

Another aspect of epithelial cell therapy relates to healing of the epithelial lining of the gastrointestinal tract to treat or prevent impaired gut function.

Polymer scaffolds are also contemplated for the purpose of facilitating replacement skin engineering, as for example described in Sheridan et al., 2000, J. Control Release 14 91 and Fauza et al., 1998, supra, as are microspheres as agents for the delivery of skin cells to wounds and burns (LaFrance & Armstrong, 1999, Tissue Eng. 5 153).

The aforementioned techniques may be readily utilized according to the present invention by use of isolated protein complexes of the invention to promote skin cell proliferation for the purposes of tissue replacement and for cosmetic skin treatments.

With regard to bone regeneration, the invention provides surgical or prosthetic implants coated, impregnated or otherwise pretreated with an isolated protein complex of the invention.

Conversely, inhibition or suppression of cell proliferation and migration by preventing or disrupting formation of IGF-IGFBP-VN complexes may constitute a prophylactic or therapeutic treatment of psoriasis or malignancies such as epithelial cancers such as breast cancer.

The invention also contemplates a method of differentiating a stem or progenitor cell by administering an isolated protein complex of the invention to said stem or progenitor cell. Isolated protein complexes comprising variant growth factors and IGFBPs may also be applicable to this method.

Differentiated cells produced according to this method may be useful in therapeutic methods such as hereinbefore described.

For example, smooth muscle cells are considered to be "mesenchymal stem cells" and may be driven to differentiate into fibroblasts, stromal cells, endothelial cells, bone or adipocytes.

In order that the invention may be readily understood and put into practical effect, particular preferred embodiments will now be described by way of the following non-limiting examples.

All competitive radioligand binding assays as described herein were performed essentially as described in Upton et al., 1999, supra.

Example 1

Competition Binding Assay to Assess Ability of Insulin, Pro-IGF-II and IGF-I to Compete with IGF-II for Binding to Vitronectin Due to the similarity in structure shared between IGFs and insulin, binding of insulin to vitronectin was examined. Crosslinking experiments performed by Upton et al., 1999, supra indicated that insulin was unlikely to compete with IGF-II for binding to vitronectin, as was the case with IGF-I. As a consequence, high concentrations of insulin were examined in order to establish whether insulin could compete with radiolabelled IGF-II for binding to vitronectin. The results shown in FIG. 1 indicated that, as for the situation originally observed with IGF-I (Upton et al., 1999, supra), insulin competed poorly with $[^{125}I]$-IGF-II for binding to vitronectin.

Investigation of IGF-I as a competitor for IGF-II binding to vitronectin revealed that IGF-I, could compete with the binding of $[^{125}I]$-IGF-II to vitronectin (FIG. 2). However, IGF-I was markedly less effective than IGF-II in competing with radiolabelled IGF-II for binding to vitronectin, requiring an approximate 3000 fold increase in IGF-I concentration above IGF-II to achieve the same effect.

Similar studies demonstrated that proIGF-II could compete with $[^{125}I]$-IGF-II for binding to vitronectin (FIG. 3). ProIGF-II was not as effective as in competing with $[^{125}I]$-IGF-II for binding to vitronectin with $IC_{50}$ values of 65.6 nM and 9.6 nM respectively. Thus, the presence of the E domain within proIGF-II represents a structural modification that alters the binding to vitronectin. This could be due to steric hindrance by the additional domain in proIGF-II compared to IGF-II, or may be a result of an altered structure of the proIGF-II molecule that alters the affinity of proIGF-II for vitronectin.

Example 2

Investigation of PAI-1 and uPAR as Competitors for Binding of IGF-II to Vitronectin PAI-1 and suPAR were investigated as molecules which might compete with IGF-II for binding to vitronectin, as these proteins have been reported to bind vitronectin (Declerck et al., 1988, J. Biol. Chem. 263 15454; Wei et al., 1994, J. Biol. Chem. 269 32380; Kanse et al., 1996, Exp. Cell Res. 224 344). At concentrations up to 2000 nM competition of PAI-1 with $^{125}I$-IGF-II for binding to vitronectin was observed with an approximate $IC_{50}$ value of 524 nM (FIG. 4). While this concentration is relatively high in terms of $IC_{50}$ values, such concentrations can be found in vivo associated with tumours (Grondahl-Hansen et al., 1993, Cancer Res. 53 2513). Indeed, Kjoller et al., 1997, Exp. Cell Res. 232 420, found 370 nM of PAI-1 was required to achieve half maximal effect in an assay assessing the ability of PAI-1 to inhibit cell migration of WISH cells. This inhibition was postulated to result via PAI-1 competing with integrins and uPAR for binding to vitronectin. Thus, the observed interaction between PAI-I, IGF-II and vitronectin may indeed have some functional consequences in vivo, particularly when IGF-II and PAI-1 levels are highly expressed as is sometimes found in tumours.

While it is known that PAI-1 binds to the N-terminal somatomedin B domain of vitronectin, the high concentrations of PAI-1 required to effectively compete with IGF-II for binding to vitronectin suggested that these studies have not provided any clear information regarding the location of IGF-II of the binding site on vitronectin. However, the results may be interpreted two ways. The first possibility is that the observed competition between IGF-II and PAI-1 is due to partial competition at the primary high affinity site on vitronectin within the somatomedin B domain via steric hindrance. Alternatively, the competition could be due to direct competition between IGF-II and PAI-1, for binding to a site on vitronectin to which PAI-1 binds with a reduced affinity. Further experimental studies are required to clarify this issue.

While the present inventors were unable to show that soluble suPAR competes for binding of IGF-II to VN, this may have been due to that fact that lyophilized suPAR was used after international transportation. There is no evidence that reconstituted suPAR is biologically active after reconstitution, although the observation that [$^{125}$I]-suPAR did not bind VN (data not shown) perhaps supports an interpretation that the suPAR used in these studies was inactive.

Use of similar techniques to those that identified the PAI-1 binding site on vitronectin to be within a fragment of vitronectin containing the 44 N-terminal amino acids (Deng et al., 1995, Thromb. Haemost. 74 66), may establish whether the competition observed between PAI-1 and IGF-II for binding vitronectin is a result of either of these possibilities.

It has previously been shown that the soluble form of the urokinase receptor (suPAR) can bind to immobilized vitronectin (Wei et al., 1994, supra). In the studies reported here, however, even at concentrations up to 300 nM, no competition between suPAR and [$^{125}$I]-IGF-II for binding to vitronectin was observed.

Example 3

Binding of IGF-I and IGF-II to Vitronectin in the Presence of Non-Glycosylated Recombinant IGFBP-3

To investigate whether IGFBPs could mediate binding of the IGFs to vitronectin, the effect of increasing concentrations of IGFBP-3 in the presence of [$^{125}$I]-IGF-I or [$^{125}$I]-IGF-II was assessed. The results are shown in FIG. 5.

At the concentrations tested, 10 ng of IGFBP-3 per well caused the greatest amount of [$^{125}$I]-IGF-I to bind to vitronectin coated wells, whereas 30 ng of IGFBP-3 per well caused the greatest amount of [$^{125}$I]-IGF-II to bind to vitronectin coated wells. The effect was most noticeable in the case of [$^{125}$I]-IGF-I, since low counts of [$^{125}$I]-IGF-I bound to vitronectin, and even at the lowest concentration of IGFBP-3 (3.7 ng), this binding was increased (FIG. 5A). Conversely, [$^{125}$I]-IGF-II did not show an increase over binding obtained on vitronectin coated wells alone, until concentrations of 11 ng/100 µL-33 ng/100 µL were reached (FIG. 5B).

Preincubation of IGFBP-3 with either [$^{125}$I]-IGF-I or [$^{125}$I]-IGF-II did not alter the binding to vitronectin as compared to the non pre-incubated concentrations of IGFBP-3 and [$^{125}$I]-IGF-I or [$^{125}$I]-IGF-II.

Example 4

Binding of IGF-I to Vitronectin in the Presence of Recombinant IGFBPs Produced in Mammalian Cells Binding assays examining the ability of [$^{125}$I]-IGF-I to bind to VN-coated dishes in the presence of IGFBPs, added at the same time as the radiolabel, were performed as described in Upton et al., 1999, supra. The data are shown in FIG. 6. Increasing amounts of IGFBP-2, -4 and -5 resulted in increased binding of labelled IGF-I to vitronectin coated wells. At the highest amount of IGFBP tested, 5 ng, binding of labelled IGF-I was increased approximately 2.8-, 3.8- and 8-fold for IGFBP-2, 4 and 5 compared to control wells where VN, but no IGFBPs, were present.

The presence of IGFBP-3 at 0.05, 0.2 and 0.5 ng/well also increased binding of labelled IGF-I to VN while 2 and 5 ng of IGFBP-3/well appeared to inhibit binding of the radiolabel. All concentrations of IGFBP-1 and -6 tested were also inhibitory.

These results demonstrate that unlike the situation with IGF-II, minimal direct binding of IGF-I to VN is observed. However, the presence of IGFBPs, especially IGFBP-2, -3, -4 and -5 enhances IGF binding to VN-coated wells, suggesting that IGFBPs mediate the binding of IGF-I to VN in this situation. In addition, the data suggests that IGFBPs have the potential to both enhance and inhibit binding of IGF-I to VN, depending on a) which IGFBPs are present and b) the amount of IGFBP present.

Example 5

Binding of Labelled IGF-I to VN in the Presence IGFBP-3 Variants

Binding assays examining the ability of [$^{125}$I]-IGF-I to bind to VN-coated dishes in the presence of an IGFBP-3 variant in which the putative "heparin binding domain" was mutated (IGFBP-3 HBD) and a variant in which glycosylation sites had been mutated (Non-gly IGFBP-3) were performed as described above. The data are shown in FIG. 7.

The IGFBP-3 glycosylation mutant used in these binding studies had three potential O-glycosylation sites at positions Asn89, Asn109, Asn172 mutated to Ala.

The IGFBP-3 HBD mutant did not enhance binding of [$^{125}$I]-IGF-I to VN-coated dishes, suggesting the heparin binding domain of IGFBP-3 is involved in binding IGFBP-3 to VN. Other studies have identified that amino acid residues outside of the putative "heparin binding domain" are responsible for IGF-I binding to IGFBP-3, hence it is most likely that the results represent decreased binding of IGFBP-3 to VN, rather than decreased binding of labelled IGF-I to IGFBP-3 (Imai et al., 2000, J Biol Chem 275:18188-18194).

Interestingly, the non-glycosylated IGFBP-3 mutant significantly enhanced binding of [$^{125}$I]-IGF-I to bind to VN-coated dishes. The striking 20-fold increase in binding of labelled IGF-I to VN-coated wells in the presence of 2 ng of the mutant IGFBP-3 is intriguing and suggests that glycosylation of IGFBP-3 inhibits interaction of either a) IGF-I to IGFBP-3 or b) IGFBP-3 with VN. Alternatively, both interactions may be hindered by the presence of carbohydrates.

Whether non-glycoslyated IGFBP-3 is functionally relevant in vivo remains to be established. Nevertheless, this finding suggests that non-glycosylated IGFBP-3 bound to VN may be a useful way to deliver IGF-I to sites where IGF-I is required to potentiate cell function such as in stimulating cell proliferation. Alternatively, non-glycosylated IGFBP-3 bound to VN may provide a mechanism for sequestering excess IGF-I in situations where cell proliferation is not required such as in tumours overexpressing IGFs.

Example 6

Competition Binding Assay Assessing Ability of IGF Variants to Compete with Labelled IGFs for Binding to VN in the Presence of Non-Glycosylated Recombinant IGFBP-3

The concentration of IGFBP3 that produced the highest binding of radiolabelled IGF depicted in FIG. 5 was used in a competition assay to determine whether increasing concentrations of IGFs and desIGFs could compete with radiolabelled IGFs for binding to vitronectin in the presence of IGFBP3. The results indicated that IGF-I, IGF-II, des(1-6) IGF-II and perhaps also des(1-3)IGF-I (not shown), at high concentrations, can compete with the binding of [$^{125}$I]-IGF-II to vitronectin in the presence of 10 ng of IGFBP3 (FIG. 8). These experimental results indicated that only IGF-I, -II and des(1-6) IGF-II could compete with IGF-II for binding to vitronectin coated wells in the presence of 30 ng of IGFBP3.

Example 7

Stimulation of Cell Proliferation by Isolated Protein Complexes Comprising IGF-II and Vitronectin The strategy of pre-binding IGF-II to VN was used in this study in an attempt to more accurately reflect the extracellular environment in vivo. Most cell culture approaches add exogenous substrates in solution phase; thereby the cells are constantly exposed to the treatments. Cells in tissues do not encounter this "constant, solution phase" environment in vivo. Thus the approach adopted for this study was to pre-bind IGFs to VN, a situation which more accurately mirrors the in vivo conditions.

Following pre-binding of IGFs to VN in culture dishes, cells were seeded into wells and the ability of IGFs complexed to VN to stimulate protein synthesis was examined by established methods (Francis et al., 1986, Biochem J. 233: 207-213). Increased protein synthesis correlates with increases in cell number, hence is a reflection of cell proliferation. Responses, expressed as percentage above control wells in which no \TN or IGFs were present, measured the incorporation of [$^3$H]-leucine into newly synthesised protein over 48 hrs.

Referring to the data in FIG. 9, when 3, 10, 30, 100, 300 and 1000 ng of IGF-II was pre-bound to the wells in the absence of VN, resulting responses of 8, 12, 10, 16, 24 and 43% above the control wells (-VN, -IGF) respectively were observed. Furthermore, these same doses of IGF-II pre-bound to VN coated wells stimulated incorporation of [$^3$H]-leucine into protein with effects of 19, 29, 39, 51, 70 and 101% respectively. Combining the responses obtained with VN alone (12%) with that obtained for IGF-II alone (refer to above) gives rise to predicted additive effects of 20, 24, 22, 28, 36 and 55% for 3, 10, 30, 100, 300 and 1000 ng of IGF-II respectively. These values are significantly different (p<0.05) to the actual effects observed when IGF-II was pre-bound to VN at all doses except for the two lowest amounts of IGF-II tested (3 and 10 ng). Thus IGF-II pre-bound to VN stimulates synergistic effects in protein synthesis ranging from 5 to 46% greater than the calculated additive effects. These responses may well be a result of the direct binding of IGF-II to VN, and may also arise from indirect binding of IGF-II to VN via IGFBPs. HaCAT keratinocytes produce large amounts of IGFBP-3 (Wraight et al., 1994, J. Invest. Dermatol 103:627-631).

Example 8

Binding of Labelled IGF-II to VN in the Presence of Recombinant IGFBPs Produced in Mammalian Cells Binding assays examining the ability of [$^{125}$I]-IGF-II to bind to VN-coated dishes in the presence of IGFBPs, added at the same time as the radiolabel, were performed as described in Upton et al., 1999, supra. The IGFBPs used in these studies were glycosylated having been produced in mammalian cells.

As shown in FIG. 10, increasing amounts of IGFBP-1, -3 and -6 resulted in decreased binding of labelled IGF-II to vitronectin coated wells in a dose-dependent manner. IGFBP-2 also appeared to compete for binding of labelled IGF-II to VN, albeit less effectively than IGFBP-1, -3 or -6. IGFBP-4 on the other hand had little effect on binding of IGF-II to \TN, while IGFBP-5 appeared to enhance IGF-II binding to a small extent. The inhibitory effect of IGFBP-3 could result from IGFBP-3 competing for binding of IGF-II to the same binding region on VN. Alternatively, or in addition, the inhibitory effect of IGFBP-3, as well as IGFBP-1 and -6. may arise from the affinity of IGF-II for VN being less than the affinity of IGF-II for these IGFBPs, hence these IGFBPs sequester IGF-II and the complex does not bind to VN.

Example 9

Stimulation of Cell Proliferation by Isolated Protein Complexes Comprising IGF-I, IGFBP-5 and Vitronectin Referring to Table 2, IGF-I with IGFBP-5 and vitronectin stimulated keratinocyte proliferation (as measured by $^3$H-leucine incorporation into newly synthesized protein) at all concentrations tested with synergistic effects observed at the highest amount tested.

It is proposed by the present inventors that the effect of isolated protein complexes upon cell proliferation may be even greater at higher concentrations of IGFBP-5 than the relatively low amount described in Table 2.

Example 10

Engineering IGF and IGFBP Variants

Amino acid residues in IGFBP-3 that are important for association with the ECM and have been defined as the putative "heparin-binding domain" are residues KGRKR at positions 228-232. Similar residues are found in the corresponding region of IGFBP-5. The IGFBP-3 HBD mutant that was used in the binding studies reported herein had the residues KGRKR altered to MDGEA based on the amino acids found in the corresponding positions in IGFBP-1. These changes result in a charge reversal in this part of the protein. This mutant still binds IGF-I and IGF-II with high affinity but binds the acid-labile subunit and the cell surface poorly (Firth et al., 1998, J. Biol. Chem. 273 2631-2638).

Heparin binding motifs in a diverse range of proteins were originally described in Cardin et al., 1989, Arteriosclerosis 9 21-32.

The C-domain of human IGF-II contains a number of positively charged amino acid residues and in particular positions 34-40 contains the amino acids RVSRRSR. Given that positively charged amino acids are important in mediating binding IGFBPs to cell surfaces and to VN, these amino acids in IGF-II may be important in binding of IGF-II directly to VN. Regardless, it would be a relatively simple procedure to introduce a "heparin binding motif" similar to that found in IGFBP-3 (BXBBB; where B is a basic amino acid; SEQ ID NO: 2) by creating an IGF-II mutant with deletions of either V$^{35}$ or S$^{36}$ along with S$^{39}$. The importance of positive residues in mediating binding of IGF-II to VN is further illustrated by the present inventors' evidence of reduced binding of the chicken IGF-II mutant, (desR$^{40}$)-IGF-II, to VN.

The C-domain of IGF-I on the other hand contains a relatively non-charged stretch of amino acids in the corresponding region of the protein to that described above for IGF-II.

This may explain why IGF-I does not bind directly to VN. In addition, insulin, which also does not bind to VN (or to IGFBPs) does not have a corresponding C-domain as it is cleaved out in the mature protein.

Human IGF-I SSSRRAPQT (SEQ ID NO: 3)

Human IGF-II RVSRRS-R (SEQ ID NO: 1)

```
Human IGF-I      SSSRRAPQT
Human IGF-II     RVSRRS--R
```

Introduction of the IGF-II sequence RVSRRSR (SEQ ID NO: 3) or the IGFBP3 sequence KGRKR (SEQ ID NO: 4) into IGF-I- could enable IGF-I to bind VN directly.

Example 11

Isolated Protein Complexes, Cell Proliferation and Survival

Bcl-2 transcription, a critical element of the cell survival pathway, is elevated in cells that attach to VN through alphav-beta3 integrins. (Matter & Ruoslahti, 2001, J. Biol. Chem. 276 27757-27763). In addition, IGF-I protects cells from apoptosis by elevating bcl-2 transcription in an AKT-dependent manner (Pugazhenthi et al., 1999, J. Biol. Chem. 274 27529-35). The IGF receptor physically associates with the alphav-beta3 integrin with a synergistic effect on cell growth (Schneller et al., 1997, EMBO J. 16 5600-5607). Thus isolated protein complexes of the invention may provide an extracellular point of integration for initiating the cell survival signals mediated by both the integrin and the growth factor receptor.

IGFBP-5 has been demonstrated to potentiate the anti-apoptotic and mitogenic effects of IGF-I in prostate cancer cells (Miyake et al., 2000, Endocrinol. 141 2257-2265). In addition, the synthesis of VN in vivo by glioma cells and in colorectal adenocarcinoma correlates with tumour grade (Uhm et al., 1999, Clin Cancer Res. 5 1587-1594; Tomasini-Johansson et al., 1994, Exp Cell Res. 214 303-312; Gladson et al., 1995, J. Cell Sci. 108 947-56; Gladson & Cheresh, 1991, J. Clin. Invest. 88 1924-32).

Hence, according to the present invention, it is proposed that IGF:IGFBP:VN complexes formed in vivo may promote tumour cell survival and progression. The invention therefore contemplates therapeutic agents that disrupt in vivo complex formation.

The heparin-binding domain of VN has been reported to inhibit fibronectin matrix assembly (Hocking et al., 1999, J. Biol. Chem. 274 27257-27264). Reduced fibronectin deposition is associated with tumour cell invasion as decreased cell migration rates are associated with increased levels of polymerised fibronectin (Morla et al., 1994, Nature 367 193-196). Hence, IGF:IGFBP complexes bound to the heparin binding domain of VN, may dampen fibronectin matrix assembly and facilitate tumour invasion of local connective tissue. Thus, the invention contemplates therapeutic agents that disrupt these in vivo complexes to reduce tumour invasiveness.

Isolated Protein Complexes and Wound Healing

The converse argument can be used to support the use of the complex in situations where cell migration is required such as in wound repair. The IGF system plays an important role in wound healing and both IGF-I and IGFBP-3 are present in wound fluid in significant concentrations. (Skottner et al., 1990, Acta Scand. Suppl. 367 63-66; Clark R (ed) 1996, Molecular and Cell Biology of Wound Repair, pp 3-50, Plenum Press, New York; Robertson et al., 1996, Endocrinol. 137 2774-2784; Vogt et al., 1998, Growth Horm. IGF Res. 8 Suppl B:107-9.

IGFBPs have been demonstrated to reduce the rate of IGF clearance from wounds. (Robertson et al., 1999, Am J. Physiol. 276 E663-71). IGFBP-3:IGF-I complexes bind to fibrin clots in vitro leading to the suggestion this also occurs in vivo, resulting in concentration of IGF-I at wound sites. (Campbell et al., 1999, J. Biol. Chem. 274 30215-30221). Similarly, vitronectin binds to fibrin (Podor et al., 2000, J. Biol. Chem. 275 19788-19794). It is also noted that vitronectin-null mice exhibit increased wound fibrinolysis and decreased microvascular angiogenesis (Jang et al., 2000, Surgery 127 696-704).

According to the present invention, it is proposed that IGFs bound to IGFBPs can bind to VN, which in turn associates with the fibrin clot, thus providing a reservoir of IGFs at the wound site. Thus isolated protein complexes of the invention could be administered to wounds to accelerate the repair process.

A particular aspect of would healing contemplated by the present invention relates to healing diabetic foot ulcers. Wound healing is delayed in diabetes. Growth factors influence the healing process and in particular, IGFs have been shown to stimulate keratinocyte proliferation. However, analysis of tissues from diabetic skin and foot ulcers reveals lack of expression of IGF-I within the basal layer and fibroblasts compared to tissue sections from non-diabetic patients. (Blakytny et al., 2000, J. Pathol. 190 589-594). Isolated protein complexes of the invention could be useful in delivery of IGF-I to these types of wounds.

Isolated Protein Complexes and Bone Engineering

IGFBP-5 facilitates binding of labelled IGF-I to bone by a mechanism that is independent of IGF receptors. (Mohan et al., 1995, J. Biol. Chem. 270 20424-20431) and enhances IGF-stimulated osteoblast function. (Andress, 1995, J. Biol. Chem. 270 28289-28296).

The implant material hydroxylapatite has been shown in numerous studies to be highly biocompatible and to osseointegrate well with existing bone. Recent evidence has found that hydroxylapatite will absorb more VN from serum than other commonly used implant materials such as titanium and stainless steel. The absorption of VN was accompanied by greater binding of osteoblast precursor cells (Kilpadi et al., 2001, J. Biomed. Mater. Res. 57 258-267).

The effect of VN on nanophase alumina vs conventional alumina was recently examined with VN being found to enhance osteoblast adhesion (Webster et al., 2001, Tissue Eng 7 291-301).

The present inventors propose that isolated protein complexes of the invention may useful as coating applied to these materials and thereby accelerate bone cell attachment, growth and integration in orthopaedic applications such as hip joint replacements.

VN enhances IGF-I stimulated osteoclastic resorption and proteinase activities in rabbit bone cell culture. (Rousselle et al., 2001, Histology & Histopathology 16 727-734) and IGFBP-5 enhances IGF-stimulated osteoblast mitogenesis. (Andress & Birnbaum, 1992, J. Biol. Chem. 267 22467-22472).

The present inventors propose that as the major IGFBP produced by bone cells is IGFBP-5, the potentiation of the IGF effect by VN is likely to also involve IGFBP-5.

Isolated Protein Complexes and Treatment of Atherosclerosis

IGF-I has previously been implicated in the development of experimental atherosclerotic lesions. Moreover, alphavbeta3 inhibitors have been demonstrated to reduce atherosclerotic lesions—this being associated with inhibition of IGF-I-mediated signaling. (Nichols et al., 1999, Circ. Res. 851040-1045).

Given that:
(i) IGFBP-5 and VN are synthesised and secreted by arterial smooth muscle cells and are present in blood vessel walls; and
(ii) IGF:IGFBP-5:VN complexes promote vascular smooth muscle cell mitogenesis and migration (Nam & Clemmons, 2000, Growth Horm. IGF Res. 10:A23);

it is proposed by the present inventors that IGF:IGFBP-5:VN complexes are involved in formation of atherosclerotic lesions. Thus therapeutic agents that disrupt complex formation may hold potential in treating atherosclerosis.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

It will also be appreciated that all patent and scientific literature and computer programs referred to are incorporated herein by reference.

TABLE 1

| Nucleic acid | Reference |
|---|---|
| IGF-I | Jansen et al., 1983, Nature 306 609 |
| IGF-II | Jansen et al., 1985, FEBS Lett 179 243 |
| IGFBP-1 | Brinkman et al., 1988, EMBO J. 7 2417 |
| IGFBP-2 | Binkert et al., 1989, EMBO J. 8 2497 |
| IGFBP-3 | Wood et al., 1988, Mol. Endocrinol. 2 1176 |
| IGFBP-4 | LaTour et al., 1990, Mol. Endocrinol. 4 1806 |
| IGFBP-5 | Kiefer et al., 1991, Biochem. Biophys. Res. Comm. 176 219 |
| IGFBP-6 | Shimasaki et al., 1991, Mol. Endocrinol. 5 938 |
| ALS | Leong et al., 1992, Mol. Endocrinol. 6 870 |
| Vitronectin | Suzuki et al., 1985, EMBO J. 4 2519 |

TABLE 2

| Treatment | −Vitronectin | +Vitronectin |
|---|---|---|
| Control | 100 ± 2.6 | — |
| IGFBP-5 | — | 109.5 ± 9.2 |
| 100 ng IGF-1 + IGFBP-5 | 117.4 ± 10.2 | 119.4 ± 1.9 |
| 300 ng IGF-1 + IGFBP-5 | 140.9 ± 2.0 | 154.3 ± 1.8 |
| 1000 ng IGF-1 + IGFBP-5 | 144.3 ± 11.0 | 161.4 ± 9.1 |

The invention claimed is:

1. A method of treating a disease or condition characterized by aberrant epithelial cell proliferation and/or migration, said method including the step of administering to a mammal an agent which disrupts an isolated protein complex comprising: insulin-like growth factor I (IGF-I); an insulin-like growth factor binding protein (IGFBP) selected from IGFBP-3 and IGFBP-5; and vitronectin; or which prevents formation of the isolated protein complex, to thereby treat said disease or condition in said mammal, wherein the agent is selected from the group consisting of IGF-II and IGF-II having a deletion or non-conservative substitution of one or more amino acid residues selected from: (i) V35; (ii) S36; and (iii) S39; of an RVSRRSR (SEQ ID NO:1) sequence at positions 34-40 in the C-domain of IGF-II.

2. The method of claim 1, wherein the disease or condition characterized by aberrant epithelial cell proliferation and/or migration is a cancer.

3. The method of claim 2, for inhibiting tumour metastasis.

4. The method of claim 2, for inhibiting tumour growth.

5. The method of claim 1, wherein the disease or condition is characterized by aberrant epithelial cell proliferation and/or migration is psoriasis.

6. The method of claim 1, wherein the disease or condition characterized by aberrant epithelial cell proliferation and/or migration is epithelial breast cancer.

7. The method of claim 1, wherein the agent is IGF-II.

8. The method of claim 1, wherein the agent is IGF-II having a deletion or non-conservative substitution of or one or more amino acid residues selected from: (i) $V^{35}$; (ii) $S^{36}$; and (iii) $S^{39}$; of an RVSRRSR (SEQ ID NO:1) sequence at positions 34-40 in the C-domain of IGF-II.

* * * * *

```
SEQUENCE LISTING

<160> NUMBER OF SEQ ID NOS: 4

<210> SEQ ID NO 1
<211> LENGTH: 7
<212> TYPE: PRT
<213> ORGANISM: Homo sapiens

<400> SEQUENCE: 1

Arg Val Ser Arg Arg Ser Arg
1               5

<210> SEQ ID NO 2
<211> LENGTH: 5
<212> TYPE: PRT
<213> ORGANISM: Artificial Sequence
<220> FEATURE:
<223> OTHER INFORMATION: Mutant Peptide
<220> FEATURE:
<221> NAME/KEY: MUTAGEN
<222> LOCATION: (1)..(1)
<223> OTHER INFORMATION: Basic Amino Acid
<220> FEATURE:
<221> NAME/KEY: MUTAGEN
<222> LOCATION: (2)..(2)
<223> OTHER INFORMATION: Any Amino Acid
<220> FEATURE:
<221> NAME/KEY: MUTAGEN
<222> LOCATION: (3)..(5)
<223> OTHER INFORMATION: Basic Amino Acid

<400> SEQUENCE: 2

Xaa Xaa Xaa Xaa Xaa
1               5
```

```
-continued

<210> SEQ ID NO 3
<211> LENGTH: 9
<212> TYPE: PRT
<213> ORGANISM: Homo sapiens

<400> SEQUENCE: 3

Ser Ser Ser Arg Arg Ala Pro Gln Thr
1               5

<210> SEQ ID NO 4
<211> LENGTH: 5
<212> TYPE: PRT
<213> ORGANISM: Artificial Sequence
<220> FEATURE:
<223> OTHER INFORMATION: IGF-I agonist C domain sequence

<400> SEQUENCE: 4

Lys Gly Arg Lys Arg
1               5
```